United States Patent [19]

Yamamoto et al.

[11] Patent Number: 4,968,487
[45] Date of Patent: Nov. 6, 1990

[54] HEAT FUMIGATION APPARATUS

[75] Inventors: Shinobu Yamamoto; Kunihiro Okada; Yoshihiro Hirobe; Ryo Yamamoto; Satoshi Ohi, all of Hiroshima; Shiro Oyama, Saitama; Yasuharu Takei, Hiroshima, all of Japan

[73] Assignee: Fumakilla Limited, Tokyo, Japan

[21] Appl. No.: 370,096

[22] Filed: Jun. 22, 1989

Related U.S. Application Data

[63] Continuation-in-part of Ser. No. 91,217, Aug. 28, 1987, abandoned.

[30] Foreign Application Priority Data

Sep. 2, 1986 [JP] Japan .................. 61-205070
Sep. 17, 1986 [JP] Japan .................. 61-141450[U]
Sep. 19, 1986 [JP] Japan .................. 61-219831
Nov. 19, 1986 [JP] Japan .................. 61-176726[U]
Apr. 17, 1987 [JP] Japan .................. 62-057531[U]

[51] Int. Cl.$^5$ .............................................. B01J 7/02
[52] U.S. Cl. ................................. 422/125; 210/504;
210/505; 210/506; 210/507; 210/508; 210/509;
210/777; 422/4; 422/305; 422/306; 422/307
[58] Field of Search .................. 422/4, 125, 305, 306,
422/307; 210/504, 505, 506, 507, 508, 509, 777;
424/76

[56] References Cited

U.S. PATENT DOCUMENTS

| | | | |
|---|---|---|---|
| 2,465,762 | 3/1949 | Supplee | 422/125 |
| 2,875,899 | 3/1959 | Allan | 210/777 |
| 4,623,462 | 11/1986 | Urig et al. | 210/508 |
| 4,663,315 | 5/1987 | Hasegawa et al. | |

FOREIGN PATENT DOCUMENTS

| | | |
|---|---|---|
| 59-62784 | 4/1984 | Japan . |
| 60-161902 | 8/1985 | Japan . |
| 60-233001 | 11/1985 | Japan . |
| 61-23163 | 6/1986 | Japan . |
| 62-45986 | 3/1987 | Japan . |

Primary Examiner—Robert J. Warden
Assistant Examiner—Timothy M. McMahon
Attorney, Agent, or Firm—Browdy and Neimark

[57] ABSTRACT

A heat fumigation apparatus for transpiring a solution of a chemical agent dissolved in a solvent by heating which comprises a container having the solution therein, a wick a part of which is immersed in the solution and a heater for heating the upper portion of the wick thereby transpiring the solution drawn up the wick. The wick is composed of an inorganic powder and/or an organic powder, a binding agent and at least one antioxidant which is substantially non-evaporative at a heating temperature.

14 Claims, 20 Drawing Sheets

FIG. 4I(A)
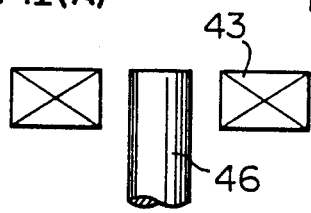
FIG. 4I(B)
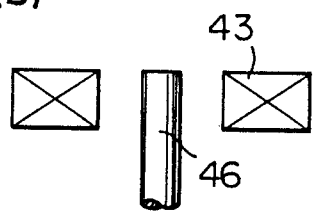
FIG. 4I(C)
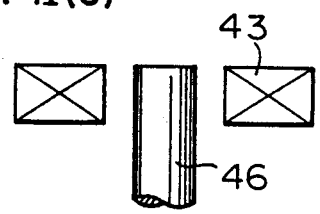
FIG. 4I(D)
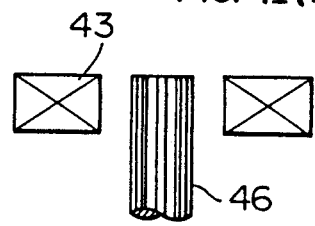
FIG. 4I(E)

HEAT FUMIGATION APPARATUS this application is a continuation-in-part of parent, co-pending application Ser. No. 07/091,217, filed Aug. 28, 1987, the contents of which are incorporated herein, said parent application Ser. No. 091,217 now being abandoned in favor of the present application.

BACKGROUND OF THE INVENTION

The present invention relates to a capillary suction type heat fumigation apparatus for drawing up a liquid chemical agent to a wick, a part of which is immersed in the liquid chemical agent, and for causing the liquid chemical agent to transpire by heating the upper portion of the wick for the purpose of insect killing, sterilization, deodorization, fragrance diffusion, etc.

Methods of killing insects by heat fumigation involving a system in which a part of a porous wick is immersed in a liquid insecticide whereby the liquid insecticide is drawn up to the wick and is caused to transpire by heating the upper portion of the wick have conventionally been known. For example, a direct heating system is disclosed in Japanese Utility Model Publication No. 25081/1968. However, since decomposition of such a insecticide is rapid in the case of direct heating, there is a general tendency to adopt an indirect heating system. As for such indirect heating systems, a method of heating a wick with a piece of felt or the like interposed between the wick and a heater is disclosed in Japanese Utility Model Publication Nos. 12459/1961 and 22585/1971, and a method of heating a wick by spacing the wick from a heater by a predetermined interval is disclosed in Japanese Utility Model Publication Nos. 26274/1968, 8361/1969, 14913/1970, 19801/1970 and 29244/1970 and Japanese Patent Publication No. 23163/1986.

Japanese Patent Publication No. 23163/1986 proposes use of a liquid insecticide which is produced by dissolving allethrin or an isomer thereof in a hydrocarbon solvent having a high boiling point in a specified range, and use of a porous wick which consists of inorganic fibers selected from porous ceramics, glass fibers, and asbestos which are bound with gypsum and/or bentonite, or a porous wick which consists of an inorganic powder body selected from kaolin, talc, diatomaceous earth, pearlite, bentonite, alumina, silica, silica alumina and titanium which is bound with starch.

In the case of the above-described heat transpiration method having a wick heating system, since the porous wick is generally made of a felt, unwoven fabric, asbestos or the like, the speed at which liquid is drawn up is comparatively high, so there is a tendency that, as the wick is heated, only the solvent in the liquid chemical agent is evaporated, thereby making it difficult to sufficiently evaporate the chemical agent, and since the high boiling point substances produced by the thermal decomposition of the chemical agent and the high boiling point substances contained in the solvent are apt to cause clogging of the wick, it is difficult to maintain stable evaporation of the chemical agent for a long time.

The use of a wick having a specified composition, in particular, a wick formed of an inorganic powder body such as that shown in Japanese Patent Publication No. 23163/1986, alleviates to some extent the problem whereby only the solvent in the liquid insecticide evaporates and stable evaporation of the insecticide is difficult, but it is still unsatisfactory. In the case of allethrin, it is required that a comparatively large amount of stock is evaporated per unit time in order to obtain a sufficient insect killing effect. Therefore, Japanese Patent Publication No. 23163/1986 proposes a method of heating the upper side surface portion of a porous wick in a comparatively high temperature range of 130° to 140° C. However, heating a wick in such a comparatively high temperature range disadvantageously accelerates the thermal decomposition or polymerization of the chemical agent, thereby reducing the amount of effective evaporation ingredient. In addition, high boiling point substances produced by the thermal decomposition or polymerization are apt to be stored in the wick, thereby causing the wick to clog.

It is known that generally in fats and oils, oxygen reacts with carbon at $\beta$ position to form hydroperoxide and generate ketone, carboxylic acid, or alcohols. When fats and oils are oxidized in this manner, they become viscous so that the heat conduction is lowered and oil foots and agglutinative substances are apt to be produced. Similarly, when a chemical agent is put into a solvent and is heated, decomposition or polymerization is caused, thereby producing agglutinative substances.

In a draw-up type heat transpiration method, since a liquid chemical agent is drawn up to a wick and the upper portion of the wick is heated to a high temperature, a phenomenon the same as or similar to the above-described phenomenon is caused, so that clogging of the wick and bad heat conduction tend to result in defective transpiration of the chemical agent. In order to improve such defective transpiration of a chemical agent caused by the decomposition or polymerization of the chemical agent due to heating, addition of an antioxidant to the chemical agent is generally suggested. For example, Japanese Patent Publication No. 12106/1979 discloses addition of BHT to a liquid chemical agent.

However, there is a close correlation between the useful life of an antioxidant and the temperature of use, and with a higher temperature, oxidation accelerates rapidly, so that a large amount of antioxidant is used, thereby greatly shortening the useful life of the antioxidant. In addition, since the antioxidant itself is thermally decomposed or evaporated depending upon the temperature condition during use, it may be lost by evaporation or may not be able to manifest antioxidant action. In order to obtain an effective antioxidant action, it is necessary to add more than a predetermined amount of antioxidant, and a large amount of antioxidant is therefore required so that the antioxidant is contained in the total liquid chemical agent.

Some antioxidants only sparingly dissolve in the solvent used, and other antioxidants do not dissolve at room temperature, thereby requiring heating for dissolution, so it is impossible to add a necessary amount of antioxidant by dissolving it.

In addition, thermal deterioration such as color change, or thermal decomposition of a wick composition (in particular, an organic powder) may occur due to friction, drying and heating during the formation of the wick or at the time of using it under heating, which tends to have a deleterious influence on the time stability and the strength of the liquid chemical agent.

SUMMARY OF THE INVENTION

Accordingly, it is an object of the present invention to eliminate the above-described problems in the prior art and to provide a heat fumigation apparatus that utilizes a wick which is capable of effectively transpiring a sufficient amount of liquid chemical agent over a long time almost without producing any thermal decomposition or copolymerization of a chemical agent at the time of using the wick under heating.

It is another object of the present invention to provide a heat transpiration apparatus that utilizes a wick which contains a small amount of antioxidant and exhibits excellent time elapsed stability and resistance to chemicals at the same time as being almost free from thermal decomposition and lowering of the strength of the wick during its formation or at the time of using it under heating.

To achieve this aim, the present invention provides a heat fumigation apparatus in which a liquid chemical agent is drawn up to a wick, a part of which is immersed in the liquid chemical agent, and the liquid chemical agent is caused to transpire by heating the upper portion of the wick, the wick being composed of at least one powder selected from the group consisting of an inorganic powder and an organic powder; a binding agent; and at least one antioxidant which does not substantially evaporate at the heating temperature during use.

BRIEF DESCRIPTION OF THE DRAWINGS

The above and other objects, features and advantages of the present invention will become clear from the following description of the preferred embodiments thereof, taken in conjunction with the accompanying drawings, in which

FIGS. 2A to 2F show another embodiment of an apparatus of the present invention, wherein FIG. 2C is a plan view thereof;

FIG. 2D is an elevational view thereof;

FIG. 2E is a side elevational view thereof;

FIG. 2A is a sectional view of the embodiment shown in FIG. 2C, taken along the line I—I;

FIG. 2B is a sectional view of the embodiment shown in FIG. 2C, taken along the line II—II; and FIG. 2F is a sectional view of the embodiment shown in FIG. 2C having a different heat receiving portion;

FIGS. 3A to 3O show still another embodiment of an apparatus according to the present invention, wherein FIG. 3A is a vertical sectional view thereof;

FIGS. 3L to 3O are explanatory views of illuminating means;

FIGS. 4A to 4K show a further embodiment of an apparatus according to the present invention, wherein FIGS. 4A and 4B are sectional views of a first example of the embodiment;

FIGS. 4C and 4D are sectional views of a second example of the embodiment;

FIGS. 4E and 4F are sectional views of a third example of the embodiment;

FIGS. 4G and 4H are sectional views of a fourth example of the embodiment;

FIGS. 4I(A) to 4I(D) show sectional views of other examples of this embodiment;

FIGS. 4I(E) is a sectional view of the wick of the example shown in FIG. 4I(D); and FIGS. 4J and 4K are elevational views of different conventional examples.

Figure 1:
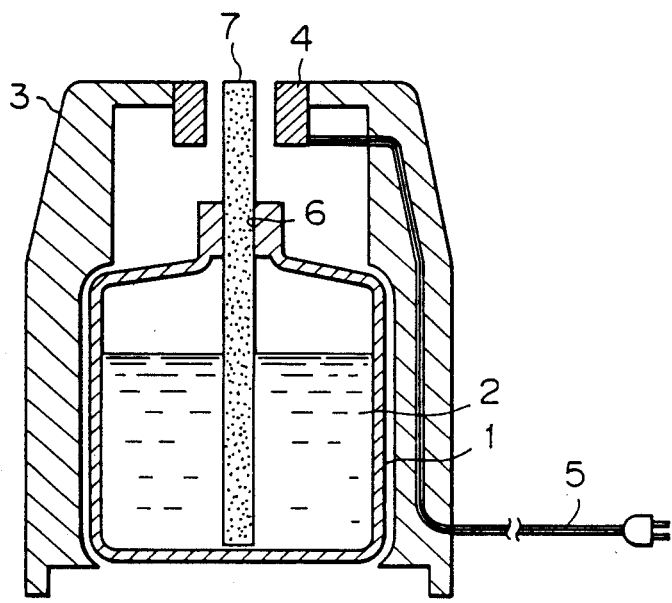
FIG. 1 is a sectional view of an embodiment of an apparatus according to the present invention.

DESCRIPTION OF THE PREFERRED EMBODIMENTS 3,5-di-t-butyl-4-hydroxytoluene (BHT) and 3-t-butyl-4-hydroxyanisole (BHA), which are known as typical examples of antioxidants, evaporate quickly than insecticides do at the heating temperature utilized in a heat transpiration method, for example, at 140° C., so that they cannot manifest any antioxidant effect. Therefore, when such an antioxidant is added to a liquid chemical agent, the solvent or the chemical agent is resinified in the wick while the liquid chemical agent is evaporated by heating and causes clogging of the wick, so that long-term stable evaporation of the chemical agent is impossible.

As a result of the studies undertaken by the present inventors, it has been found that if a specific compound to be described later, namely, an antioxidant which is substantially non-evaporative at the heating temperature employed during use (e.g., about 110° to 140° C. in the case of a heating transpiration insect killing system) is mixed and bonded with the wick itself, the above-described problem does not occur, that the antioxidant effect is manifested by addition of an extremely small amount of antioxidant as compared with the addition of an antioxidant to the liquid chemical agent, and that not only can the thermal deterioration of the wick during the formation of the wick and/or at the time of using it under heating be prevented, but that thermal decomposition or polymerization of the chemical agent at the time of using it while heating the wick, resinification of the chemical agent by oxidation and, hence, clogging of the wick can also be prevented, thereby maintaining sufficient evaporation of the chemical agent over a long time.

A wick in accordance with the present invention is produced by kneading a mixture of an inorganic powder and/or an organic powder, a binding agent, and a later-described specific antioxidant with an appropriate amount of water, and extrusion molding and drying it. It goes without saying that another molding means such as pressure molding may also be adopted.

Various methods may be adopted for adding and binding the specific antioxidant. Since the wick composition is influenced by heat during the formation of the wick, for example, friction heat in extrusion molding, friction heat in pressure molding and drying heat in the drying process, and, further, since it is heated for a long time during the evaporation of the liquid chemical agent under heating for use, thermal deterioration of the wick composition is a critical problem. In particular, the thermal deterioration of an organic powder or a binding agent exerts a deleterious effect on the stability of a chemical agent, and the strength, color change and resistance to chemicals of the wick. However, addition of the specific antioxidant can prevent the thermal deterioration of the wick composition during the formation of the wick and at the time of using it under heating. Furthermore, even in the case of an antioxidant which does not dissolve or only sparingly dissolves in a solvent, it is possible to allow the chemical agent to contain a sufficient and effective amount that is greater than the amount which will dissolve by mixing and binding it with the wick composition. Even in the case of an antioxidant which only sparingly dissolves at room temperature, mixing and binding it with the wick composition enables it to thermally dissolve in the inner portion of the wick while the wick is being used under heating, and to manifest its antioxidant effect.

A molded wick for use in the present invention is microporous and the amount of liquid chemical agent drawn up is quite small in comparison with a wick that mainly consists of fibrous substances. Thus, it is suitable as a wick for long-term use.

As the main material for the wick, at least one powder selected from the group consisting of inorganic powders such as clay, talc, kaolin, diatomaceous earth, gypsum, pearlite, bentonite, acid clay, volcanic stone, glass fiber and asbestos; and organic powders such as wood powder, activated charcoal, cellulose, pulp, linter and polymeric resins is used. Among these, an inorganic powder is preferred and, in particular, gypsum, clay, diatomaceous earth, acid clay and pearlite are preferable in terms of moldability.

As for the binding agent, carboxymethylcellulose (hereinunder referred to as "CMC"), starch, acacia gum, gelatin, polyvinyl alcohol (hereinunder referred to as "PVA"), etc. are usable. Among these, CMC is preferable in terms of its non-solubility in a solvent and its moldability. A wick produced by binding at least two of the abovedescribed inorganic powders with CMC or a mixture of CMC with gelatin or PVA and molding the wick composition is the most preferable. In such case, the amount of liquid insecticide drawn up depends upon the amount of binding agent (CMC) mixed in. Therefore, a suitable amount of binding agent for mixing in is between 1 wt % and 25 wt %, inclusive, with due consideration given to the draw-up properties and moldability of the wick.

Other additives such as a pigment, dyestuff and antiseptic agent may be added to a porous wick, as and when necessary, provided that the properties of the wick are not impaired.

The antioxidant which is incorporated into the wick composition is an antioxidant which is substantially non-evaporative at the heating temperature utilized during use, e.g., 140° C. The following compounds are usable as such antioxidant.

Compound A: stearyl-$\beta$-(3,5-di-t-butyl-4-hydroxphenyl)propionate
Compound B: 2,2'-methylene-bis(4-methyl-6-t-butylphenol)
Compound C: 2,2'-methylene-bis(4-ethyl-6-t-butylphenol)
Compound D: 4,4'-methylene-bis(2-methyl-6-t-butylphenol)
Compound E: 4,4'-methylene-bis(2,6-di-t-butylphenol)
Compound F: 4,4'-butylidene-bis(3-methyl-6-t-butylphenol)
Compound G: 4,4'-thiobis(3-methyl-6-t-butylphenol)
Compound H: 1,3,5-trimethyl-2,4,6-tris(3,5-di-t-butyl-4-hydroxybenzyl)benzene
Compound I: 1,1,3-tris(2-methyl-5-t-butyl-4-hydroxyphenyl)butane
Compound J: tetrakis[methylene(3,5-di-6-butyl-4-hydroxycinnamate)]methane
Compound K: N,N'-hexamethylenebis(3,5-di-t-butyl-4-hydroxy-hydrocinnamamide)
Compound L: 1,6-hexanediol-bis-[3-(3,5-di-t-butyl-4-hydroxyphenyl)propionate]
Compound M: triethyleneglycol-bis[3-(3-t-butyl-5-methyl-4-hydroxyphenyl)propionate]
Compound N: 2,2-thio-diethylenebis[3-(3,5-di-t-butyl-4-hydroxyphenyl)propionate]
Compound O: N,N'-bis[3-(3,5-di-t-butyl-4-hydroxyphenyl) propionyl]hydrazine
Compound P: tris-(3,5-di-t-butyl-4-hydroxybenzyl)-isocyanurate
Compound Q: 2,4-bis-(n-octylchio)-6-(4-hydroxy-3,5-di-t-butylanilino)-1,3,5-triazine
Compound R: 2,2-chiobis(4-methyl-6-t-butylphenol)
Compound S: 3,5-di-t-butyl-4-hydroxybenzylphosphonate diethylester These compounds may be used either singly or in the form of a mixture of two or more compounds. The amount of compound used is 0.02 to 3 wt %, preferably 0.005 to 1 wt % of the total amount of wick composition. If the amount of compound added is too small, the above-described effects of the addition of the antioxidant such as the prevention of thermal deterioration during the formation of the wick or at the time of it being used under heating are difficult to obtain.

It is also possible to use dilauryl thiodipropionate (hereinunder referred to as DLTP) and distearyl thiodipropionate (hereinunder referred to as DSTP), which are antioxidants generally known as peroxide decomposers, in combination with the antioxidant according to the present invention. Addition of such a peroxide decomposer enables decomposition of any peroxide produced at the time when the wick is used under heating, for example, an agglutinative substance which causes clogging of the wick, and enables stable evaporation to be maintained over a long time.

A heat fumigation apparatus according to the present invention is capable of transpiring a chemical agent such as an insecticide, disinfectant, germicide, deodorant and perfume under heating for the purpose of insect killing, germ killing, deodorization, fragrance diffusion, etc.

As the liquid chemical agent, a liquid insecticide, a perfume, etc. may be used, depending upon the purpose. When an apparatus of the present invention is used as a heat transpiration insect killing apparatus, a liquid insecticide is put into a container, and a heater is energized to heat the surface of the wick to a temperature preferably in the range of 110° to 140° C. in accordance with the kind of insecticide being utilized. If the heating temperature is too high, thermal decomposition or polymerization of the chemical agent is likely to result, thereby lowering the amount of effective evaporation ingredient, so that the high-boiling point substances produced are unfavorably stored in the wick and tend to cause clogging of the wick.

As the liquid insecticide, solutions consisting of various insecticidal components dissolved in various aliphatic hydrocarbon solvents are usable. However, use of a single aliphatic unsaturated hydrocarbon solvent unfavorably emits a foreign odor, and an aliphatic saturated hydrocarbon solvent is the most preferable. It dose not matter if an aliphatic unsaturated hydrocarbon is contained in an amount which will not lead to the above-described inconvenience. Even in the case of using an aliphatic saturated hydrocarbon solvent, if it contains 19 carbon atoms or more, it has a high viscosity or assumes a gel state or a solidified state, so it is impossible for the liquid insecticide to be smoothly drawn up to the wick. It is therefore necessary that the number of carbon atoms be restricted to 18 or less. On the other hand, since there is a tendency for the total effective evaporation ratio of the insecticidal ingredient to become lower as the number of carbon atoms decreases, it is necessary that the number of carbon atoms be at least 12 in order to obtain a sufficient evaporation ratio. However, there is no problem in incorporating an aliphatic hydrocarbon beyond the above-described range if the quantitative ratio does not lead to the above-described inconveniences.

As examples of aliphatic saturated hydrocarbons that are usable in the present invention, dodecane ($C_{12}$), tridecane ($C_{13}$), tetradecane ($C_{14}$), pentadecane ($C_{15}$), hexadecane ($C_{16}$), heptadecane ($C_{17}$), octadecane ($C_{18}$) and mixtures thereof may be cited, and commercially available solvents containing such an aliphatic hydrocarbon as the main ingredient, for example, No. 0 Solvent H (produced by Nippon Oil Company, Limited), No. 0 Solvent M (produced by Nippon Oil Company, Linited), Normal Paraffin (produced by Mitsuishi Texaco Chemical Co., Ltd.), and IP Solvent 2028 (produced by Idemitsu Petro-Chemical Co., Ltd.) are also usable.

Various kinds of conventional evaporating insecticidal components may be used in the present invention. For example, pyrethroid insecticides, carbamate insecticides and organic phosphorus insecticides are usable. Pyrethroid insecticides such as those mentioned in the following are preferably used in general because of their high safety properties.

3-allyl-2-methylcyclopenta-2-en-4-on-1-yl dl-cis/-trans-chrysanthemate [general name: allethrin, trade name: Pynamin, produced by Sumitomo Chemical Co., Ltd. (hereinunder referred to as PA)]

3-allyl-2-methylcyclopenta-2-en-4-on-1-yl d-cis/-trans-chrysanthemate [trade name: Pynaminforte, produced by Sumitomo Chemical Co., Ltd. (hereinunder referred to as PB)]

d-3-allyl-2-methylcyclopenta-2-en-4-on-1-yl d-transchrysanthemate [trade name: Exthrin, produced by Sumitomo Chemical Co., Ltd. (hereinunder referred to as PC)]

3-allyl-2-methylcyclopenta-2-en-4-on-1-yl d-transchrysanthemate [general name bioallethrin (hereinunder referred to as PD)]

2-methyl-4-oxo-3-(2-provinyl)cyclopenta-2-enylchrysanthemate (hereinunder referred to as PE)

N-(3,4,5,6-tetrahydrophthalimide)-methyl dl-cis/-trans-chrysanthemate [general name: phthalthrin, trade name: Neopynamine, produced by Sumitomo Chemical Co., Ltd. (hereinunder referred to as PF)]

5-benzyl-3-furylmethyl d-cis/trans-chrysanthemate [general name: resmethrin, trade name: Chrysronforte, produced by Sumitomo Chemical Co., Ltd. (hereinunder referred to as PG)]

5-(2-propagyl)-3-furylmethyl chrysanthemate [general name: furamethrin (hereinunder referred to as PH)]

3-phenoxybenzyl-2,2-dimethyl-3-(2',2'-dichloro)-vinylcyclopropane carboxylate [general name: permethrin, produced by Sumitomo Chemical Co., Ltd. (hereinunder referred to as PI)]

3-phenoxybenzyl-d-cis/trans-chrysanthemate [general name: phenothrin, trade name Smithrin, produced by Sumitomo Chemical Co., Ltd. (hereinunder referred to as PJ)]

α-cyanophenoxybenzyl isopropyl-4-chlorophenyl acetate [general name: fenvalerate, trade name: Smiciden, produced by Sumitomo Chemical Co., Ltd. (hereinunder referred to as PK)]

(S)-α-cyano-3-phenoxybenzyl(1R,cis)-3-(2,2-dichlorovinyl)2,2-dimethylcyclopropane carboxylate [general name: cypermethrin f (hereinunder referred to as PL)]

(R,S)-d-cyano-3-phenoxybenzyl (1R,1S)-cis/trans-3-(2-2-dichlorovinyl)-2,2-dimethyl cyclopropane carboxylate [general name: cypermethrin (hereinunder referred to as PM)]

α-cyano-3-phenoxybenzyl d-cis/trans-chrysanthemate [general name: cyphenothrin (hereinunder referred to as PN)]

1-ethynyl-2-methyl-2-pentenyl-cis/transchrysanthemate [general name: empenthrin (hereinunder referred to as PO)]

3-allyl-2-methyl-cyclopenta-2-en-4-on-1-yl-2,2,3,3tetramethylcyclopropane carboxylate [general name: terallethrin (hereinunder referred to as PP)]

1-ethynyl-2-methyl-2-pentenyl-2,2,3,3-tetramethylcyclopropane carboxylate (hereinunder referred to as PQ)

1-ethynyl-2-methyl-2-pentenyl-2,2-dimethyl-3-(2,2-dichlorovinyl)cyclopropane-1-carboxylate (hereinunder referred to as PR)

[(pentafluorophenyl)-methyl]-1R,3R-3-(2,2-dichloroethynyl)-2,2-dimethyl-cyclopropane carboxylate [general name: Fenfulthrin (hereinunder referred to as PS)]

An appropriate concentration of the effective insect-killing ingredient is 0.5 to 10 wt %, preferably 0.5 to 8.0 wt %.

Similarly, when an apparatus of the present invention is used for the purpose of diffusing fragrance, various natural and artificial perfumes may be used. There are, for example, animal base and vegetable base natural perfumes, and artificial perfumes such as hydrocarbons, alcohols, phenols, aldehydes, ketones, lactones, oxides and esters, and these perfumes may be used either singly or in the form of a mixture of two or more perfumes In addition, various kinds of chemical agents such as deodorants, germicides and repellents are usable, depending upon the purpose, so long as they are chemical agents which are evaporated by heating. The concentration of such a chemical agent is preferably 0.5 to 10 wt %.

As described above, the present invention has the following advantages:

since a wick used in the present invention contains a specific antioxidant, the apparatus of the present invention scarcely produces any clogging of the wick due to thermal decomposition or polymerization of the ingredients of a chemical agent when the wick is being used under heating, thereby producing a high evaporation ratio and maintaining effective and stable evaporation over a long time;

since an antioxidant which does not substantially evaporate at the heating temperature employed during use is added when the wick is produced, not only are thermal deterioration of the wick during the formation of the wick or at the time of using it under heating and lowering of the wick's strength and resistance to chemicals prevented, but also the amount of antioxidant to be added for preventing thermal decomposition, polymerization or the like of the chemical agent efficiently and effectively is very small in comparison with that which occurs in the case of adding an antioxidant directly to the chemical agent itself;

even in the case of an antioxidant which does not dissolve or only sparingly dissolves in a solvent, it is possible for the chemical agent to be made to contain a sufficient and effective amount that is greater than the amount which will normally dissolve by mixing and binding it with the wick composition; and even in the case of an antioxidant which only sparingly dissolves at room temperature, mixing and binding it with the wick composition enables it to thermal dissolve in the inner portion of the wick while the wick is being used under heating, and to manifest its antioxidant effect.

Explanation of Porosity

The porosity of a wick used in the present invention will here be explained.

The present inventors have found that by producing a wick of a draw-up type heat fumigation apparatus by molding an inorganic powder and/or an organic powder and a binding agent into a porous body having a porosity of 25 to 40%, it is possible to prevent leakage of liquid when the inner pressure of the container is raised due to changes in the ambient temperature or pressure or when the apparatus tumbles over, and sufficient evaporation is possible at a comparatively low temperature, thereby producing scarcely any thermal decomposition of the chemical agent and maintaining stable transpiration at a high effective evaporation ratio over a long period.

that is, reduction of the porosity of the wick and restriction of the permeability thereof prevent leakage of liquid which may be caused when the liquid is forced up from the inside of the container due to the difference in pressure between the inside and outside or when the immersing liquid is pushed out of the wick To state this more concretely, when a difference between the inner pressure and the outer pressure occurs due to thermal expansion of the interior of the container because of the radiant heat produced by the heater when it is heated for use or a reduction in the ambient pressure while the apparatus is left unused or is being used, and this difference in pressure forces the liquid in the container upwards, if the porosity of the wick is reduced, the pores are filled with the liquid which serves as a barrier, and the increased frictional resistance which occurs between the wick material and the liquid suppresses the tendency of the liquid to be forced up due to the pressure differential, thereby restraining the liquid from being forced up in a state in which the inner pressure is slightly higher and, hence, preventing leakage.

If the prevention of such leakage alone is aimed at, the smaller is the porosity, the better. However, in the case of a wick used for a draw-up type heat transpiration apparatus, it is also necessary to consider the rise of the inner pressure of the container due to heating, and stable and effective transpiration of a liquid chemical agent.

It has been found that in order both to prevent this leakage and to ensure that the liquid chemical agent transpires stably and effectively over a long period, it is necessary to restrict the porosity of the wick to a range of 25 to 40%.

A porous wick of the present invention is produced, for example, by adding a binding agent having a particle diameter of not more than 100 $\mu$m, such as starch or carboxymethylcellulose (CMC), to an inorganic powder having a particle diameter of not more than 100 $\mu$m, further adding an appropriate amount of water, kneading the mixture, and extrusion molding and drying the mixture. Needless to say, other molding methods may also be adopted.

The thus-obtained porous wick is an ultra microporous one and has a smaller porosity than the type of wick that mainly consists of fibrous substances or of an ordinary inorganic powder bound with starch. Furthermore, the amount of liquid chemical agent drawn up is quite small, so that it is suitable as a wick for long term use.

In order to restrict the porosity of a wick to the above-described range, it is preferable that the inorganic powder, organic powder and binding agent are all powders having a small particle diameter. The particle diameter of each ingredient powder is preferably not more than 100 $\mu$m.

The relationship between each material and the porosity of the wick produced was examined The porosities of the wicks molded from various combinations of inorganic and organic powders are shown in Table 1.

TABLE 1

| Composition | No. 1 | No. 2 | No. 3 | No. 4 | No. 5 | No. 6 | No. 7 | No. 8 | No. 9 |
| --- | --- | --- | --- | --- | --- | --- | --- | --- | --- |
| Inorganic powder | | | | | | | | | |
| Gypsum | — | — | — | — | 8 | 8 | — | 10 | 15 |
| Clay | 6 | — | — | 6 | 4 | 5 | 8 | — | — |
| Diatomaceous earth | — | 5 | 10 | — | 4 | — | — | 5 | — |
| Pearlite | 6 | 5 | — | 7 | — | 2 | — | — | — |
| Organic powder | | | | | | | | | |
| Foamed polymer | — | — | — | — | — | — | 2 | — | — |
| Activated charcoal | — | — | — | 1 | — | 0.5 | — | — | — |
| Wood powder | 2 | 4 | 2 | — | — | — | — | — | — |
| Binding agent | | | | | | | | | |
| Starch | 3 | 2 | 2 | — | — | — | 5 | — | — |
| CMC | — | — | 0.5 | 1.2 | 0.5 | 0.3 | 0.5 | — | 1.0 |
| PVA | — | — | — | — | — | — | — | 0.5 | — |
| Porosity (%) | 52 | 65 | 65 | 60 | 42 | 34 | 31 | 39 | 21 |

The main reasons why porosity will increase are, for example, (a) that a wick is molded only from powders having a large particle diameter;

(b) that a wick contains a large amount of porous powder such as diatomaceous earth, wood powder, charcoal, volcanic ash, pearlite (foaming is broken); and (c) that a wick contains a large amount of continuous cellular resin powder.

The term "pore" does not include a mere hollow portion of a hollow body.

As described above, if the porosity of a porous wick is reduced, the amount of liquid drawn up will also be reduced. Therefore, insufficient porosity leads to a decrease in the amount of evaporation. When the porosity is less than 25%, a problem in practical use will occur. On the other hand, if a large amount of porous powder is contained, the porosity will increase and leakage tends to be produced. When the porosity is more than 40%, the result is unfavorable in terms of practical use.

As described above, if a wick has a specific porosity, leakage is prevented even if the pressure of the interior of a container is raised with a rise in ambient temperature or a change in atmospheric pressure, or even if the container tumbles over. Thus there is no danger of staining the vicinity of the position where the apparatus stands. Furthermore, since the apparatus is capable of transpiring a sufficient amount of the effective ingredient of a chemical agent as a comparatively low heating temperature, hardly any clogging of the wick due to thermal decomposition or copolymerization of the chemical ingredient, in particular, the insect-killing ingredient, is caused. Thus a high effective evaporation ratio is obtainable, and it is possible to maintain effective and stable evaporation over a long period.

Preferred embodiments of the apparatus according to the present invention will be explained hereinunder with reference to the accompanying drawings.

FIG. 1 is a sectional view of an embodiment of an apparatus according to the present invention. A container 1 having a liquid chemical agent 2 therein is removably accommodated in and held by a casing 3. The upper portion of the casing 3 is kept open, and an annular heater (or a pair of semiannular heaters) 4 is fixed to the open portion. The reference numeral 5 denotes a chord connected to the heater 4. An inlet 6 for introducing a liquid chemical agent is provided at the upper portion of the container 1, and a wick 7 is held by the inlet 6 in such a manner that the wick 7 substantially serves as a stopper and the upper portion of the wick 7 is disposed at the central portion of the annular heater 4.

FIGS. 2A to 2F show another embodiment of an apparatus according to the present invention.

An apparatus body 21 is composed of a main body 22 and a cover 23, and the main body 22 is composed of an upper body 24 and a lower body 25 which is removably connected to the upper body 24. A recess 26 adapted to accommodate a bottle is formed at the bottom 24a of the upper body 24. A lower lamp cover 28 and an upper lamp cover 29 of a lamp 27 are attached to the recess 26 and the side surface 24b of the upper body 24, respectively. The lower body 25 has a configuration and a size which allows the lower body 25 to be engaged with the recess 26 when the former is slidingly inserted into the latter. On the side surface 25a of the lower body 25, a hook retainer 211 which engages a hook 210 formed on the lower lamp cover 28 is provided. An annular bottle receiver 214 which engages the lower small-diameter portion 213 of a bottle 212 is integrally provided on the bottom surface 25b of the lower body 25.

The bottle 212 has substantially the same configuration as that of the recess 26, and a wick 216 is supported by a plug 215 which is fitted into the upper small-diameter portion 212a of the bottle 212. The lower portion of the wick 216 is immersed in a liquid chemical agent in the bottle 212. A plurality of bottle supporters 217 are provided in the recess 26 in such a manner as to come into contact with the shoulder portion 212b of the bottle 212 and hold the bottle 212 so that it does not move at all. A clearance 218 is formed between the shoulder portion 212b and the recess 26 in such a manner as a communicate with the outside through an annular space 219 between the peripheral wall of the lower large-diameter portion 212c of the lower body 25 and the lower vent holes 220 formed at the bottom portion of the lower body 25.

The cover 23 is cylindrical and is mounted on the cylindrical upper portion 24c of the upper body 24 such that an annular space 222 is formed between the cover 23 and an annular heater 221 which is attached to the center of the upper portion 24c. A large-diameter transpiration hole 223 which is concentric with the heater 221 is formed at the upper portion of the cover 23 At the lower portion of the transpiration hole 223, a cap-shaped heater receiver 224 having a substantially annular side vent hole 225 between the heat receiver 224 and the transpiration hole 223 is provided, and a center vent hole 226 is formed at the center of the heat receiver 224. The annular space 222 communicates with the outside through vent holes 222a.

The upper portion of the wick 216 faces the heater 221 from a hole 227 formed at the bottom portion 26a of the recess 26 such that a peripheral gap 228 is formed between the hole 227 and the wick 216 and a peripheral gap 229 is formed between the wick 216 and the heater 221. The peripheral gap 228 communicates with a space 230 between the upper body 24 and the recess 26, the space 230 in turn communicating with the annular space 222 at upper vent holes 231 and with the annular space 219 at lower vent holes 232.

Figure 2A:
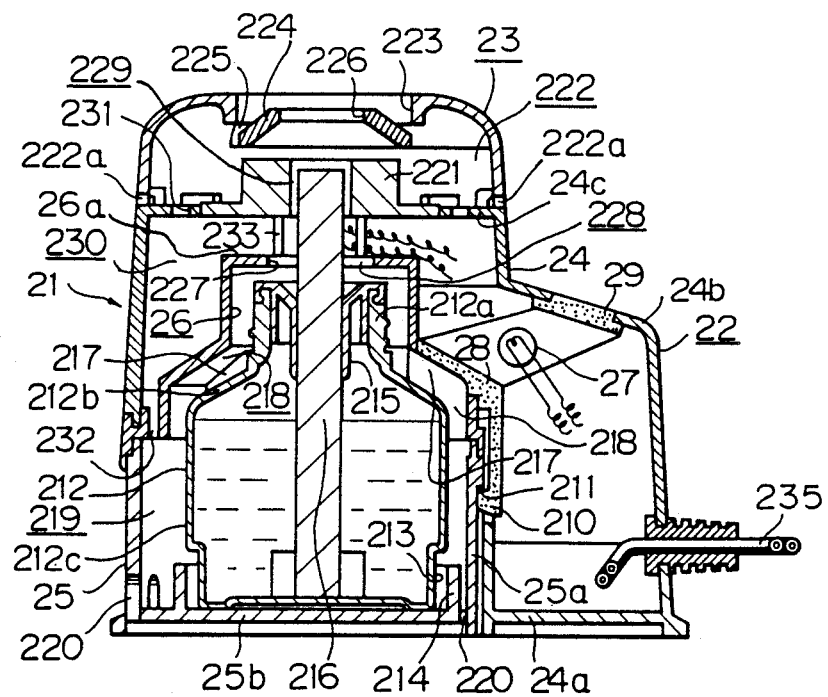
Figure 2B:
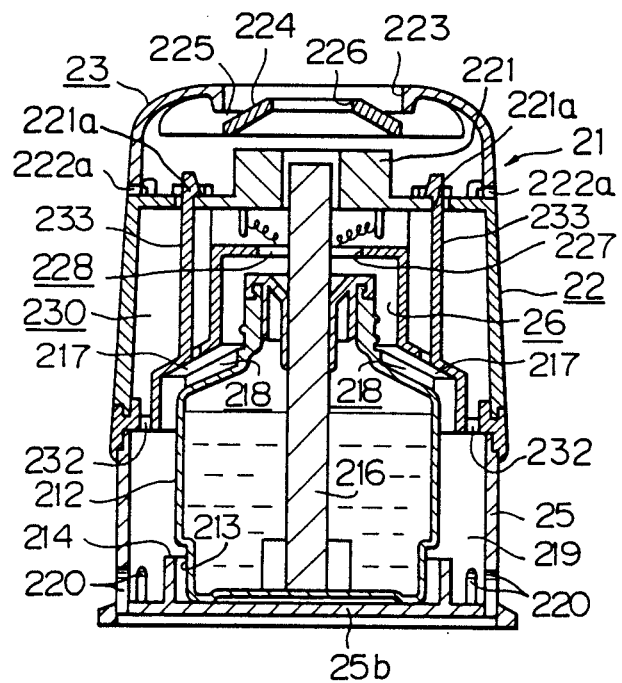
Figure 2C:
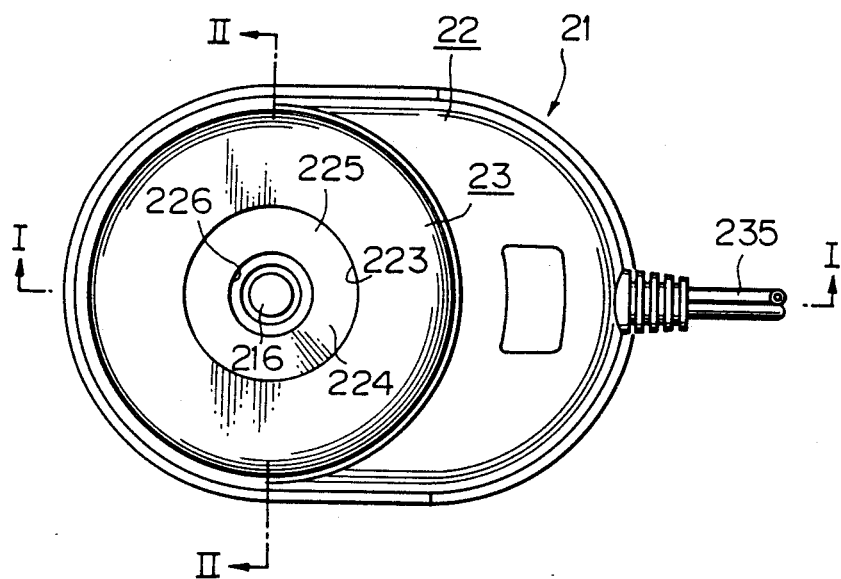
Figure 2D:
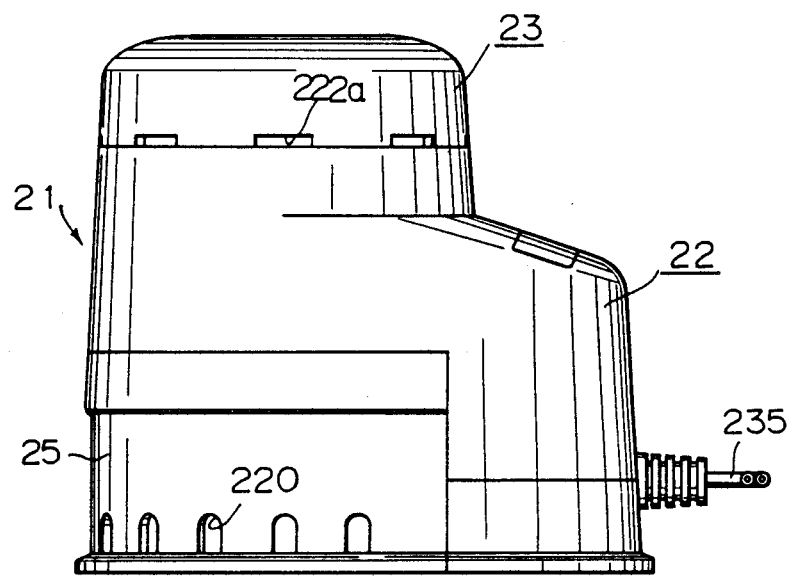
Figure 2E:
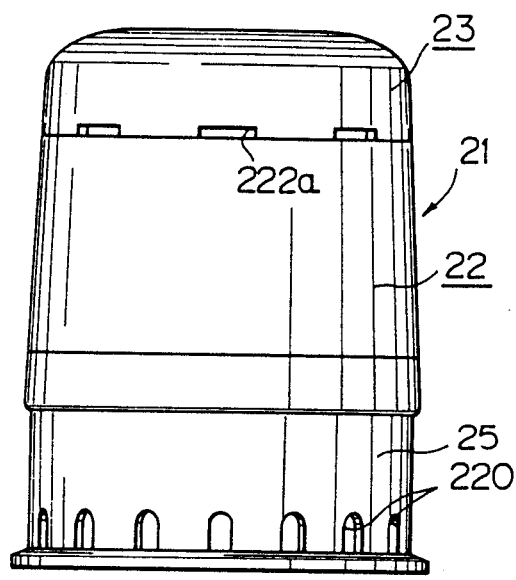

The heater 221 is attached to the upper portion 24c of the upper body 24 by engaging pieces 233 which are integrally provided with the recess 26 with retaining portions 221a of the heater 221, as shown in FIG. 2B.

The bottle 212 is attached to the bottle receiver 214 of the lower body 25 by fitting the small-diameter portion 213 of the bottle 212 into the bottle receiver 214. The lower body 25 is connected to the upper body 24 by sliding and inserting the lower body 25 into the upper body 24 such that the bottle 212 is accommodated in the recess 26 and engaging the hook retainer 211 with the hook 210.

When the lead 235 is connected in this state to the power source to allow the lamp 27 to be turned on, the lamp 27 can be observed with the eye through the upper lamp cover 29 and it illuminates the bottle 212 through the lower lamp cover 28. In other words, not only can the liquid surface within the bottle 212 be discerned by the illumination but also the lamp 27 has an illumination effect which can be seen through the bottle 212 and the lower cover body 25. For this purpose, the lower and upper lamp covers 29 and 28, the bottle 212 and the lower body 25 are made of light transmitting materials.

At the same time, the heater 221 is energized to heat the upper portion of the wick 216, whereby the chemical agent in the liquid chemical agent drawn up from the bottle 212 is transpired and evaporated through the transpiration hole 223 to the outside, and the heat receiver 224 is heated by the preheating and the raised heat of the heater 221.

When the heater 221 is energized, an upward air flow is produced by the heat and the ambient air flows into the apparatus body 21 in the following way:
(1) lower vent holes 220→annular space 219→clearance 218→peripheral gap 228→peripheral gap 229 and upper vent holes 231→central vent hole 226→and side vent hole 225→transpiration hole 223.

In this way, since the ambient air flows around the bottle 212, the bottle 212 is cooled, thereby suppressing the rise in temperature of the interior of the bottle 212 and preventing leakage of the liquid chemical agent from the wick 216 due to the rise in inner pressure, and it is possible to release the chemical agent transpired below the heater 221 smoothly to the outside without any fear of the main body 22 being filled with the remaining chemical agent.

The ambient air flows in the following way:

(2) lower vent holes 220→annular space 219→clearance 218→peripheral gap 228→peripheral gap 229→annular space 222→side vent hole 225→transpiration hole 223.

The ambient air flows in the following way:

(3) lower vent holes 220→annular space 219→lower vent hole 232→space 230→upper vent holes 231→annular space 222→side vent hole 225 and central vent hole 226→transpiration hole 223.

The ambient air flows in the following way:

(4) vent holes 222a→annular space 222→side vent hole 225 and central vent hole 226→transpiration hole 223.

Figure 2F:
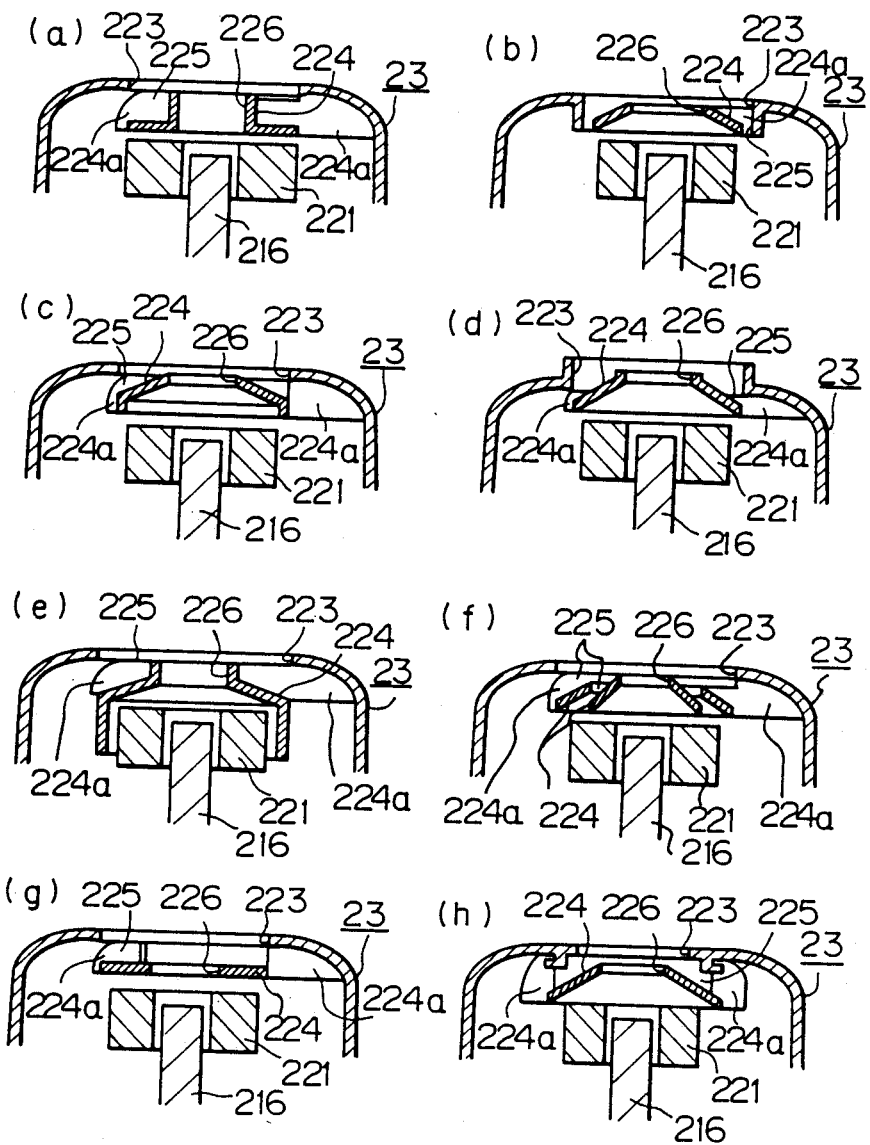

Examples of the configuration of the heat receiver 224 are shown in FIGS. 2F(a) to 2F(h). The heat receiver 224 may be attached to the cover 23 through ribs 224a.

In other words, the heat receiver 224 may have any configuration so long as at least a part of it is provided on the heater 221 and has vent holes at its central part and around its periphery. These vent holes may have any configuration, for example, the central vent hole may be circular, polygonal, or star-shaped, and the vent holes around the heat receiver 224 may be slit-like, circular or annular. Furthermore, if at least a part of the heat receiver 224 is provided on the heater 221, it may have a structure in which radiant heat is further received from the side portion of the heater or the like.

The range of temperature within which no adhesion of a given chemical agent is likely to be caused differs according to the particular kind of chemical agent. If the apparatus is used as an electric mosquito killer, and a chemical agent consisting of an aliphatic hydrocarbon solution containing a general pyrethroid insecticide such as allethrin, phenothrin, framethrin or prallethrin is used, the temperature of the heat receiver 224 is maintained at 60° C., preferably not lower than 70° C.

For this purpose, it is possible to heat the heater 221 to a high temperature. The appropriate temperature of the heater 221 is 70° C. to 450° C.

For example, if the heater 221 heated to 120° to 130° C. is used, it is possible to maintain the temperature of the heat receiver 224 at not lower than 70° C. by maintaining a gap of less than 10 mm, preferably less than 5 mm between the heater 221 and the under surface of the heat receiver 224.

The heat receiver 224 may be integrally provided with the cover 23 by adoption of a bridge or the like. In this case, it is possible to lower the heat conducted from the heat receiver 224 to the cover 23 and, hence, to suppress the potential for heat conduction to the cover 23 by making the bridge narrow or keeping the heat receiver 224 and the cover 23 a predetermined distance apart from each other by a suitable arrangement with such a bridge.

Alternatively, it is possible to make the heat receiver 224 separately from the cover 23, and to fix the heat receiver 224 to the cover 23, heater 221 and the apparatus body 21 by adhesion, welding, screw- or press-fitting, or the like.

The heat receiver 224 may be made of any material capable of resisting the heat produced during use. For example, metals such as aluminum, stainless steel, copper and brass, ceramics such as alumina, glass and porcelain, polymeric resins such as phenol resin, nylon resin and polypropylene resin are usable.

The configuration of the heater 221 is not limited to a ring-form. It may also have a U-shaped configuration, or a combination of a plurality of heaters may be used.

The heat receiver 224 does not necessarily have a flat surface; it may have a curved surface or a surface provided with a bridge for joining the heat receiver 224 to the cover 23, a rib for commutating upward air flow, and also a small vent hole.

The cover 23 may be provided integrally with the upper body 24.

The configuration of the apparatus body 21 and the bottle 212 are not restricted to those adopted in this embodiment, and may have other forms.

The upper body 24 and the lower body 25 may be fitted in other ways apart from the sliding manner illustrated.

Since the heat receiver 224 is situated within the transpiration hole 223 and at least above the heater 221, the heat radiated from the heater 221 rises and first hits the heat receiver 224, and thereafter rises further to the outside through each vent hole and the transpiration hole 223. Thus, most of the heat radiated from the heater 221 is absorbed by the heat receiver 224, which becomes hot and the vicinity of the heat receiver 224 such as the upper surface is warmed by the radiant heat, thereby producing an keeping warm effect. Therefore, an upward air flow from the vent holes to the transpiration hole 223 through the apparatus body 21 is naturally produced.

On the other hand, the chemical agent caused to transpire by heating transpires from the vicinity of the heating portion of the heater 221 due to the upward air flow of the chemical agent itself, and the above-described upward air flow produced by the heat is added thereto at the heat receiver 224, thereby accelerating the transpiration further upward. The chemical agent therefore passes through each air vent hole and transpires upwardly from the transpiration hole 223, while the keeping warm effect of the heat receiver 224 prevent the transpired agent from being cooled and condensing.

Even if the chemical agent comes into contact with the heat receiver 224, since the heat receiver 224 is hot, the chemical agent does not adhere thereto. The reason for this is that when a transpired chemical agent is rapidly cooled by coming into contact with a cold wall or the like, the chemical agent condenses and adheres to the wall, but when it comes into contact with a warm portion, such adhesion does not occur.

Furthermore, even if the cover 23 is spaced a considerable distance from the heater 221, it is possible for the chemical agent to evaporate from the transpiration hole 223 without adhesion to the interior of the apparatus if the height of the heat receiver 224 which is good in heat conduction is increased.

Since the heat receiver 224 is disposed within the transpiration hole 223 at a position below the upper surface of the cover 23, even if a wind blows from the side, it is unlikely to hit the heat receiver 224 directly such as to cool it. Even if a side wind does hit the heat receiver 224, since the heat receiver 224 is hot, it is unlikely to be cooled significantly. Thus, the above-described phenomenon of adhesion of the chemical agent caused by rapid cooling of the heat receiver 224 by a side wind is unlikely to be produced. Furthermore, since at least two-fold upward air flows are produced by heat from the vent holes at the center and in the vicinity of the heat receiver 224, thereby constituting double upward air flows flowing from the transpiration hole 223 to the outside, any influence of a side wind or any disturbance in the atmosphere on the transpiration of the chemical agent is greatly suppressed.

For the above-described reasons, the transpired chemical agent does not adhere to the vent hole portions such as to reduce the area through which the chemical agent passes and, hence, the amount of chemical agent transpired, so that the expected effect of the chemical agent is adequately attained. Since the heat receiver 224 absorbs much heat, the temperature of the upper surface in the vicinity of the transpiration hole 223 does not rise much, so that overheating is prevented and the danger of burns is reduced. In addition, since the transpired chemical agent does not remain within the apparatus body 21, it does not adhere to the interior of the apparatus body 21, thereby obviating the need for regular disassembly and cleaning of the apparatus.

As described above, since it is possible to maintain the upper surface of the cover 23 at a low temperature, even if the distance between the cover 23 and the heater 221 is shortened and the total height of the apparatus body is made low, it is possible to maintain the temperature of the upper surface of the cover 23 within the range specified by the Electric Appliance Control Law.

More specifically, the Electric Appliance Control Law of Japan regulates the temperature of the outer surface of the shell of an electric fumigating insecticide which is used at 100 V, stating that it should not be higher than 70° C. In a conventional apparatus, since it is necessary to have the cover spaced a good distance away from the heater in order to maintain the ambient temperature of the chemical agent transpiring portion at not higher than 70° C., the total height of the apparatus becomes high. In contrast, in a heat fumigation apparatus of this embodiment, even if the distance between the cover and the heater is shortened, it is possible to maintain the ambient temperature of the chemical agent transpiring portion at not higher than 70° C.

FIGS. 3A to 3O show still another embodiment of an apparatus according to the present invention.

FIG. 3A is a vertical sectional view of a heat fumigation apparatus of this embodiment. The reference numeral 31 represents an apparatus body provided with a bottle receiver 32. The front portions of the bottle receiver 32 and a peripheral wall portion 34 constitutes an opening portion 33. A window 35 is formed on the back surface of the peripheral wall portion 34. An opening 37 is formed on the upper surface 36 of the bottle receiver 32. A heater supporter 38 is provided on the upper surface 36 on the upper peripheral side of the opening 37. A heater 39 is attached to the heater supporter 38 and a wick hole 310 is formed in the heater 39.

A lamp 311 is provided within the apparatus body 31 behind the window 35. A vent hole 313 is provided on the upper surface 312 of the apparatus body 31 above the heater 39. A mounting hole 314 is provided in the upper surface 312 and a light introducing member 315 consisting of a transparent resin is inserted in the mounting hole 314. The lower end of the light introducing member 315 has an inclined surface 315*a* which faces the lamp 311.

The bottle receiver 32 accommodates a bottle 316. The bottle 316 contains a transpiring liquid chemical agent 317 such as an insecticide, repellant, deodorant, germicide and perfume, and a wick 318 is inserted into a mouth 316*a* of the bottle 316. The lower portion of the wick 318 is immersed in the liquid chemical agent 317, while the upper portion of the wick 318 is inserted into the wick hole 310 of the heater 39.

The heater 39 and the lamp 311 are energized to operate the heater 39 and turn on the lamp 311. The heat of the heater 39 transpires the liquid chemical agent 317 drawn up to the wick 318 and emits it to the outside through the vent hole 313.

In this case, since the body portion 316*b* of the bottle 316 is in direct contact with the ambient air due to the presence of the opening portion 33, cooling, which serves to reduce the thermal effect produced by the heater 39 at the time when it is being used under heating, is promoted. Therefore, any leakage due to a rise in the inner pressure during heating is prevented, thereby improving the thermal stability of the liquid chemical agent 317.

Since the light from the outside shines directly upon the body portion 316*b* of the bottle 316, it is possible to observe the amount of liquid (liquid surface) in the bottle with the naked eye.

When the lamp 311 is turned on, light is thrown on the bottle 316 through the window 35. Therefore, the amount of liquid (liquid surface) is clearly discerned in the light due to a difference between the refractive index of light in the liquid chemical agent 317 and that in the air layer.

The light of the lamp 311 is thrown to the outside through the light introducing member 315, thereby serving as an illumination.

FIGS. 3B and 3C show a modification of this embodiment. The apparatus body 31 of the heat fumigation apparatus is composed of an upper container 320 and a lower container 321. The lower container 321 is provided with the bottle receiver 32. The front portions of the bottle receiver 32 and a peripheral wall portion 34 constitute the opening portion 33. An insertion hole 323 and a plurality of retaining holes 324 situated in front and to the rear of the insertion hole 323 are provided on the upper surface 322 of the lower container 321. In the lower container 321 directly under the insertion hole 323, a lower contact 325 is provided through a supporting member 325*a*. The lower contact 325 is connected to a power source lead 326, which is led out of the lower container 321.

The upper container 320 is provided with a bottle upper portion receiver 327 and a heater supporter 328 to which a heater 329 is attached. The heater 329 is situated above the bottle upper portion receiver 327 and is provided with a wick hole 330. A retaining projection 332 and an upper contact 333 are provided on the lower surface 331 of the upper container 320. A switch 335 is attached to the peripheral wall portion 334 of the upper container 320. One terminal 335*a* of the switch 335 is connected to the upper contact 333 through a lead wire 336, and the other terminal 335*b* of the switch is connected to the heater 329 and the lamp 343 through lead wires 337 and 338, respectively. A vent hole 339 is provided in the upper surface of the upper container 320. Windows 341 and 342 are provided on the shoulder portion 340 of the bottle upper portion receiver 327 and the heater supporter 328, respectively.

The bottle 316 is placed on the receiver 32 of the lower container 321 and the retaining projection 332 of the upper container 320 is retained by the retaining hole 324 of the lower container 321, thereby connecting the upper and lower containers 320 and 321 to each other. At this time, the upper contact 333 is connected to the lower contact 325, and the upper portion of the bottle 316 is inserted into the bottle upper portion receiver 327, while the wick 318 is inserted into the wick hole 330 of the heater 329.

When the switch 335 is turned on, the heater 329 is energized and the lamp 343 is turned on The heater 329 heats the wick 318, thereby transpiring the liquid chemical agent 317. The transpired liquid chemical agent 317 is emitted from the vent hole 339 to the outside.

In this case, since the body portion 316b of the bottle 316 is in direct contact with the ambient air due to the presence of the opening portion 33, cooling, which acts to reduce the thermal effect produced by the heater 329 at the time when it is used under heating, is promoted. Therefore, any leakage due to the rise in the inner pressure during heating is prevented, thereby improving the thermal stability of the liquid chemical agent 317.

Since the light from the outside shines directly upon the body portion 316b of the bottle 316, it is possible to observe the amount of liquid (liquid surface) in the bottle with the naked eye.

When the lamp 343 is turned on, light is thrown onto the bottle 316 through the window 341. Therefore, the amount of liquid (liquid surface) is clearly discerned in the light due to a difference between the refractive index of light in the liquid chemical agent 317 and that in the air layer, so that it is possible to discern the amount of liquid (liquid surface) either in the dark or in the light. The lamp 311 also has a illuminating effect.

The amount of exposure of the body portion 316b of the bottle 316 is preferably 10 to 100%, more preferably 20 to 100% of the girth of the body portion 316b with a view to facilitating visibility.

Figure 3A:
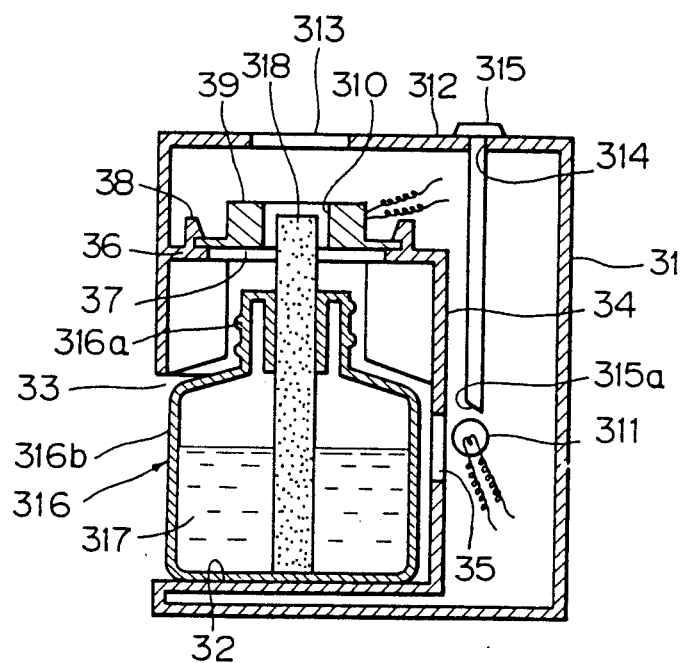
Figure 3B:
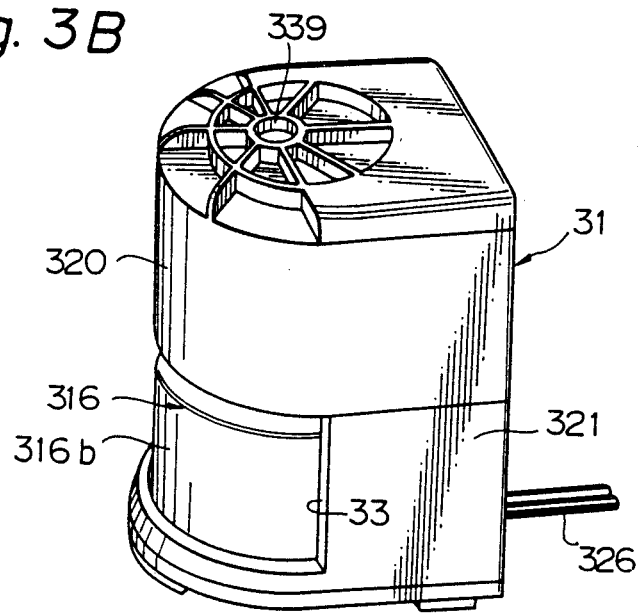
FIG. 3B is a perspective view of a modification of the embodiment shown in FIG. 3A.
Figure 3C:
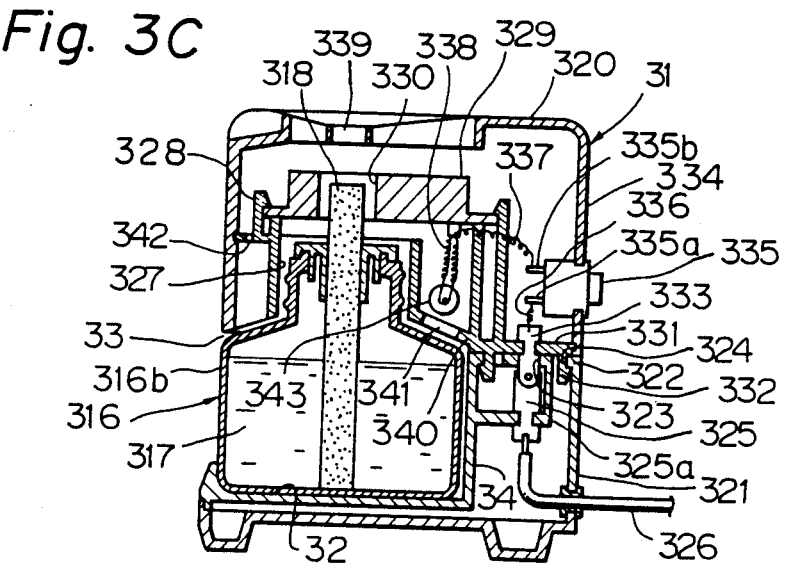
FIG. 3C is a vertical sectional view of the modification shown in FIG. 3B.
Figure 3D:
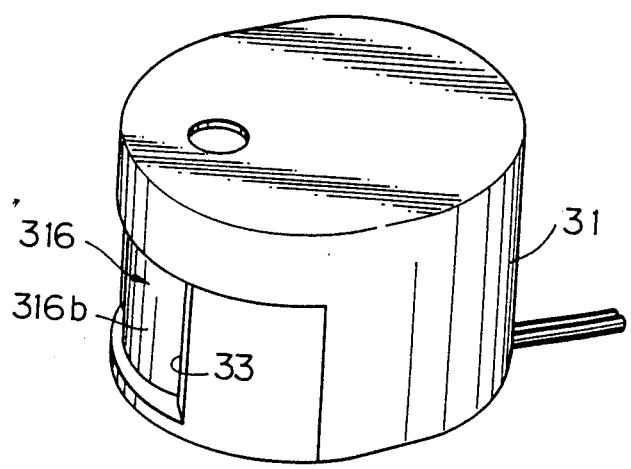
FIGS. 3D to 3I are respectively perspective views of different modifications of the embodiment shown in FIG. 3A.

For example, in the apparatus shown in FIG. 3D, the opening portion 33 is provided on the apparatus body 31 so as to communicate with the bottle receiver 32, and about 20% of the girth of the body portion 316b of the bottle 316 is exposed.

Figure 3E:
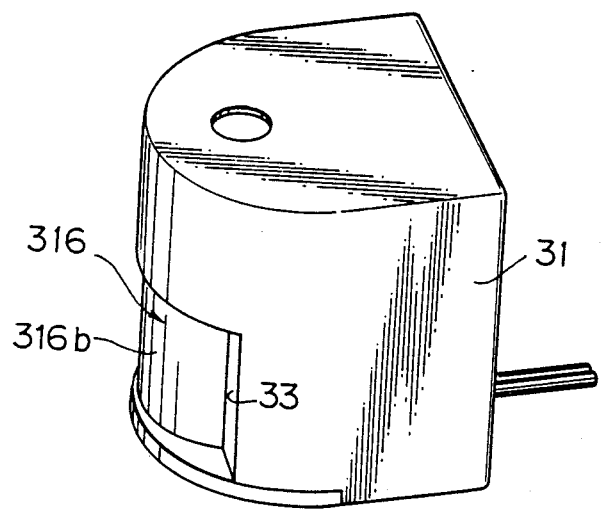

In the heat fumigation apparatus shown in FIG. 3E, about 50% of the girth of the body portion 316b of the bottle 316 is exposed from the opening portion 33.

Figure 3F:
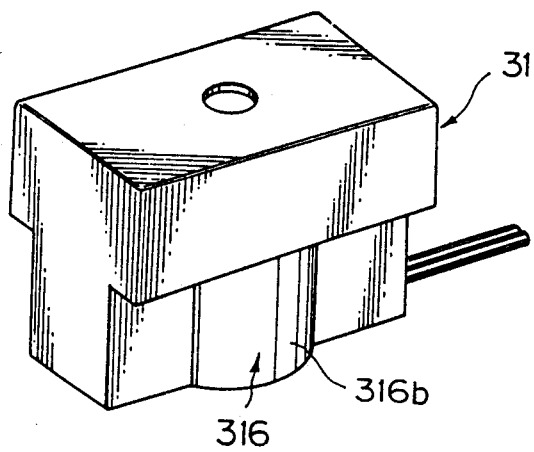

In the heat fumigation apparatus shown in FIG. 3F, about 60% of the girth of the body portion 316b of the bottle 316 is exposed.

Figure 3G:
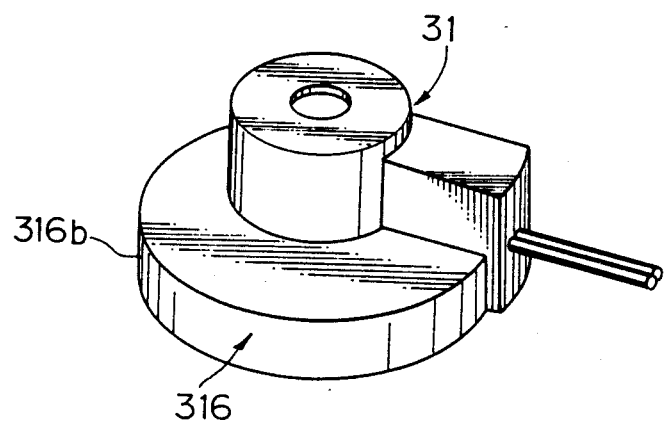
Figure 3H:
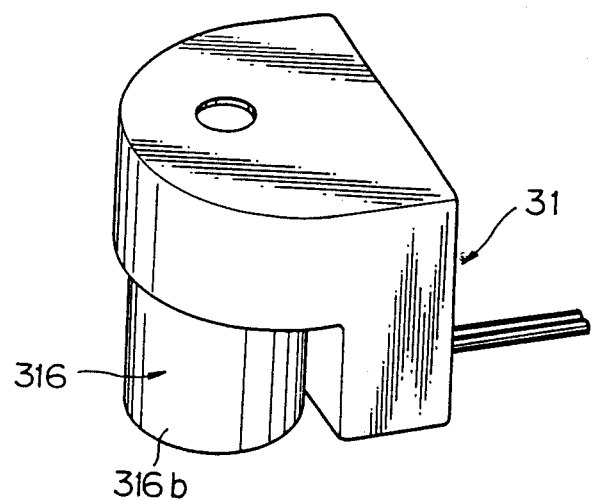
Figure 3I:
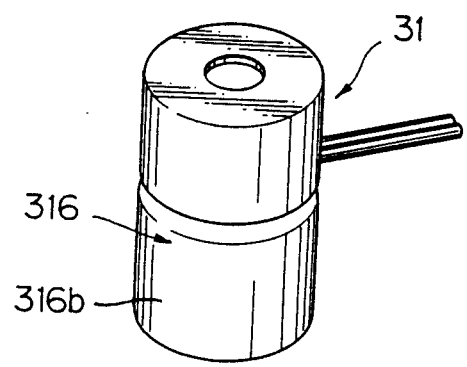

In the heat fumigation apparatus shown in FIG. 3G, about 90% of the girth of the body portion 316b of the bottle 316 is exposed, while in the heat fumigation apparatuses shown in FIGS. 3H and 3I, about 100% of the girth of the body portion 316b of the bottle 316 is exposed.

Figure 3J:
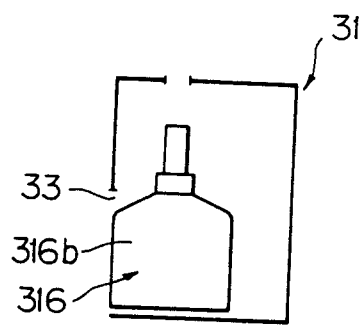
FIGS. 3J and 3K are explanatory views of the size of an opening.
Figure 3K:
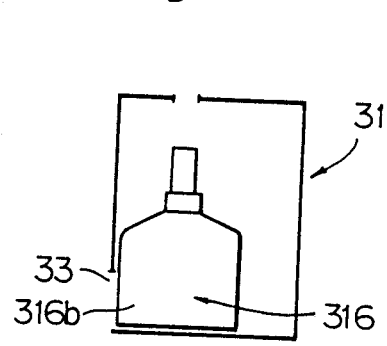
Figure 3L:
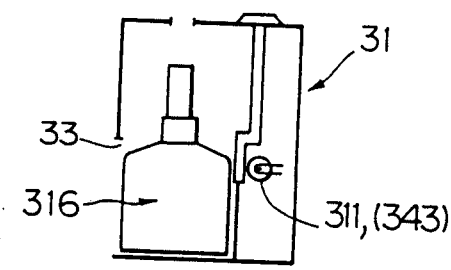
Figure 3M:
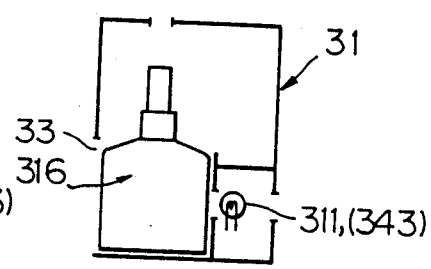
Figure 3N:
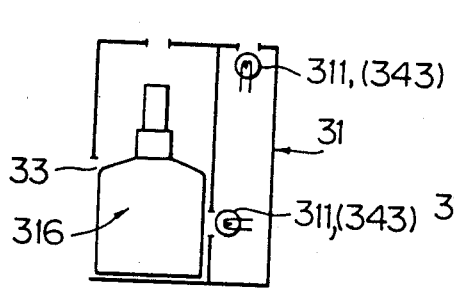
Figure 3O:
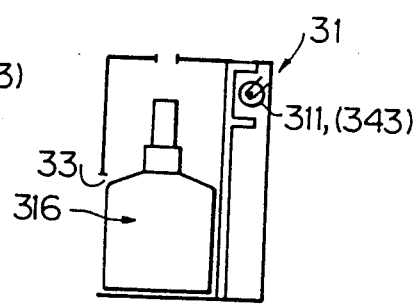

The opening portion 33 of the apparatus body 31 may have a size which allows a section comprising both the upper portion and the lower portion of the bottle 316 to be seen, as shown in FIG. 3J, or a section comprising the middle portion and the lower portion of the bottle 316 to be seen, as shown in FIG. 3K.

The lamps 311 and 343 may employ any system such as illumination by refraction of light (utilizing optical fibers or the optical path of transparent resins), direct illumination and reflecting illumination, so long as its structure is capable of illuminating the bottle 316 at least from the interior. The number of the lamp 311 (343) may be two or more (see FIGS. 3L, 3M, 3N and 3O). It is also possible to provide a switching circuit exclusively for the lamps 311 and 343 so that the lamps may be turned on as desired.

Another option is to incorporate an ultraviolet absorber in the material of which the bottle 316 is made in order to screen ultraviolet rays and increase the time stability of the liquid chemical agent 317.

In addition, vent holes or gaps may be provided in the apparatus body 31, thereby further enhancing the transpiring and cooing efficiency of the liquid chemical agent 317.

As described above in detail, an apparatus of this embodiment is a heat fumigation apparatus composed of an apparatus body accommodating a bottle provided with a wick which draws up a liquid chemical agent and a heating means provided within the apparatus body for heating the wick and transpiring a liquid chemical agent, characterized in that the apparatus body is provided with a bottle exposing means for exposing at least a part of the body portion of the bottle and an illuminating means for illuminating the liquid surface of the bottle.

Accordingly, since at least a part of the body portion of the bottle is exposed, the body portion is in direct contact with the ambient air and cooling which serves to reduce the thermal effect produced by the heater when being used under heating is promoted. Therefore, any leakage due to a rise in the inner pressure during heating is prevented, thereby improving the thermal stability of the liquid chemical agent.

Furthermore, since the light easily enters the bottle from the outside, the amount of liquid (liquid surface) can be clearly discerned due to a difference between the refractive index or reflectivity of light in the air layer and that in the liquid chemical agent layer, so that it is easy to observe the amount of remaining liquid chemical agent with the naked eye.

Since the lighting means shines upon the liquid surface of the bottle, the amount of liquid (liquid surface) is clearly visible in the light due to a difference between the refractive index of light in the liquid chemical agent and that in the air layer. In addition, since the liquid surface is seen from the outside, it is easier to observe the amount of remaining liquid chemical agent in the dark. This lighting means further serves as an illumination which is visible even in the dark.

FIGS. 4A to 4K show a further embodiment of an apparatus according to the present invention.

Figure 4A:
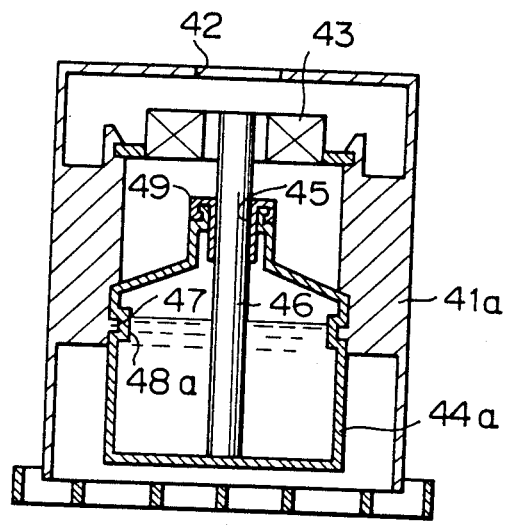
Figure 4B:
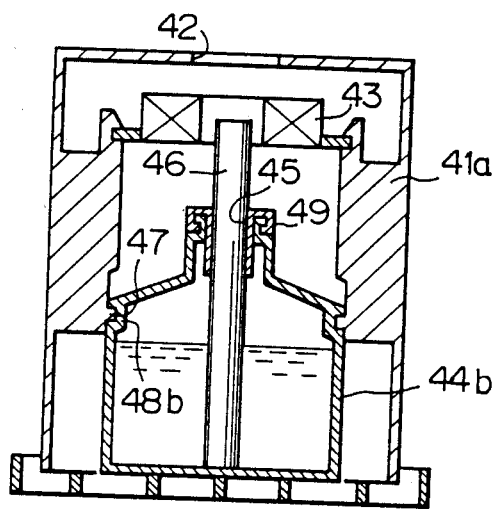

In FIGS. 4A and 4B, the reference numeral 41a represents an outer container having a transpiration hole 42 at the upper portion thereof. A cylindrical heater 43 is secured to the upper portion of the outer container 41a below the transpiration hole 42. The reference numerals 44a and 44b denote liquid chemical agent tanks accommodated in the lower portion inside the outer container 41a. An inlet 45 which allows a liquid chemical agent to be poured therethrough is provided at the upper portion of each of the liquid chemical agent tanks 44a and 44b, and a wick 46 is inserted into the inlet 45 in such a manner as to serve as a stopper. The wick 46 protrudes from the inlet 45 by a predetermined length, and the lower end portion of the wick 46 is brought into contact with the bottom of the liquid chemical agent tank 44a or 44b.

A retaining portion 47 for retaining the liquid chemical agent tanks 44a and 44b in the vertical direction is provided within the outer container 41a.

On the outer peripheries of the liquid chemical agent tanks 44a and 44b, engaging portions 48a and 48b are respectively provided in such a manner as to be removably engaged with the retaining portion 47. The engaging portions 48a and 48b are provided at vertically different positions. The engaging portion 48a of the liquid chemical agent tank 44a shown in FIG. 4A is provided at a lower position than the engaging portion 48b. The reference numeral 49 denotes a plug for fixing the wick 46 to the inlet 45.

In the above-described structure, the two liquid chemical agent tanks 44a and 44b are exchangeably mounted on the outer container 41a. In other words, both liquid chemical agent tanks 44a and 44b are mounted on the outer container 41a by removably engaging the respective engaging portions 48a and 48b with the retaining portion 47.

At this time, the retaining positions of the liquid chemical agent tanks 44a and 44b with respect to the heater 43 are relatively changed depending upon the positions of the engaging portions 48a and 48b. More specifically, the liquid chemical agent tank 44a with the engaging portion 48a provided at a lower position is held at a relatively high position, as shown in FIG. 4A. Therefore, the wick 46 is fitted into the heater 43 to a sufficient depth. On the other hand, the liquid chemical agent tank 44b with the engaging portion 48b provided at a higher position is held at a relatively low position, as shown in FIG. 4B. Therefore, the wick 46 is fitted into the heater 43 to a shallow position. In this way, by using each of the liquid chemical agent tanks 44a and 44b having the engaging portions 48a and 48b at different positions, the position of the wick changes with respect to the heater 43, whereby the heating area of the wick 46 and, hence, the amount of liquid chemical agent evaporated varies.

Figure 4C:
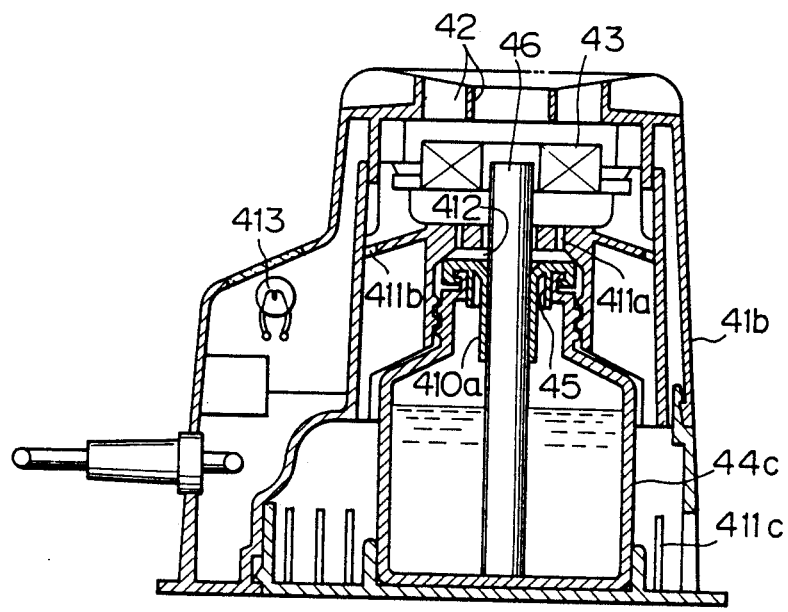
Figure 4D:
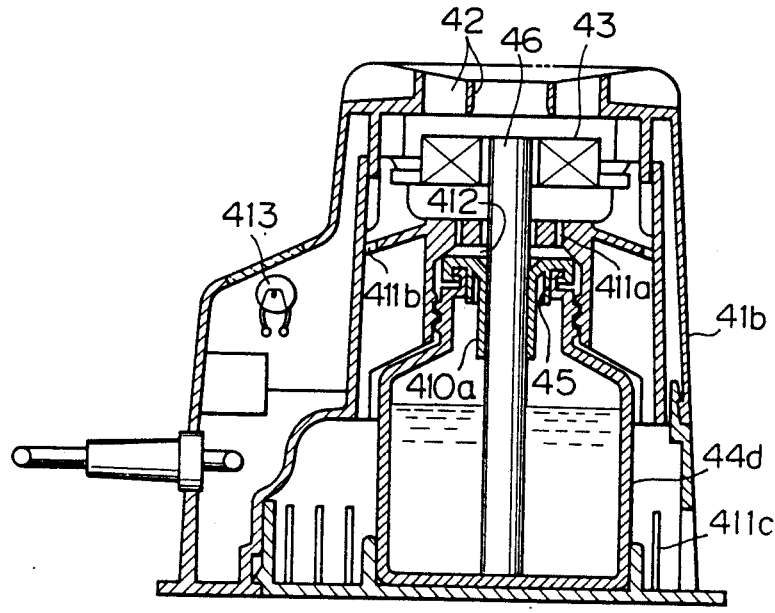

FIGS. 4C and 4D show a modification of this embodiment. In FIGS. 4C and 4D, the reference numeral 41b represents an outer container having a transpiration hole 42 at the upper portion thereof. The cylindrical heater 43 is secured to the upper portion of the outer container 41b below the transpiration hole 42. The reference numerals 44c and 44d denote liquid chemical agent tanks accommodated in the lower portion inside the outer container 41b. The inlet 45 through which a liquid chemical agent may be poured is provided at the upper portion of each of the liquid chemical agent tanks 44c and 44d, and the wick 46 is inserted into the inlet 45 in such a manner as to serve as a stopper through plugs 410a. The wicks 46 inserted into the respective liquid chemical agent tanks 44c and 44d project from the inlet by respectively different lengths, so that by exchanging the liquid chemical agent tanks 44c and 44d with respect to the outer container 41b, the opposing depths with respect to the heater 43 vary.

In FIGS. 4C and 4D, the reference numerals 411a, 411b and 411c denote vent holes, 412 a liquid well, and 413 is an indicating lamp adapted to show when the heater 43 is energized.

Figure 4E:
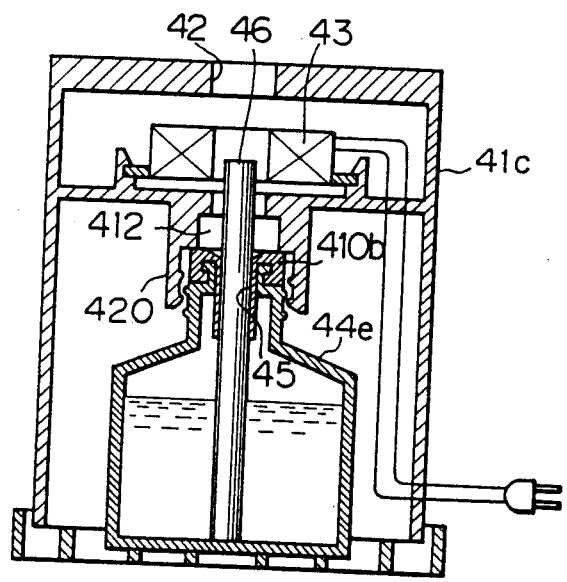
Figure 4F:
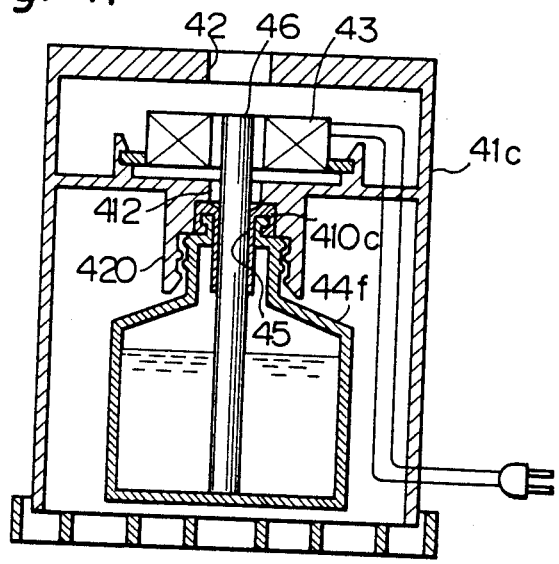

FIGS. 4E and 4F show another modification. The reference numeral 41c represents an outer container having a transpiration hole 42 at the upper portion thereof. The cylindrical heater 43 is secured to the upper portion of the outer container 41c below the transpiration hole 42. The reference numerals 44e and 44f denote liquid chemical agent tanks accommodated in the lower portion inside the outer container 41c An inlet 45 through which a liquid chemical agent may be poured is provided at the upper portion of each of the liquid chemical agent tanks 44e and 44f, and the wick 46 is inserted into the inlet 45 in such a manner as to serve as a stopper through a plug 410b or 410c. The liquid chemical agent tanks 44e and 44f are mounted on the outer container 41c by engaging the outside of the mouth portion of the liquid chemical agent tanks 44e and 44f with a retaining portion 420 of the outer container 41c. The plugs 10b and 410c have different configurations, whereby the mounting positions of the liquid chemical agent tanks 44e and 44f are made vertically different from each other. Therefore, by exchanging the liquid chemical agent tanks 44e and 44f, the depths to which the wicks 46 are inserted into the heater 43 may be changed.

Figure 4G:
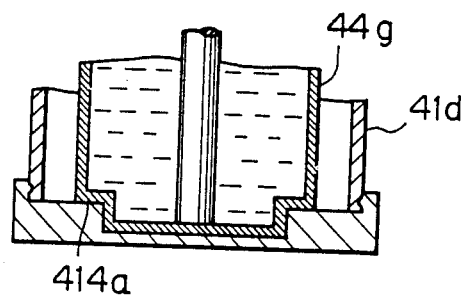
Figure 4H:
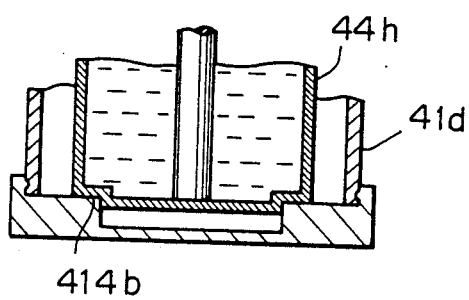
Figure 4J:
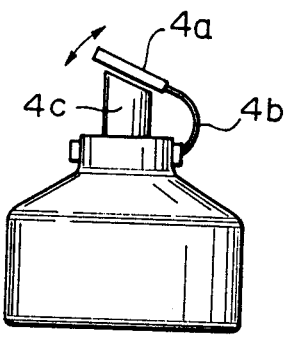
Figure 4K:
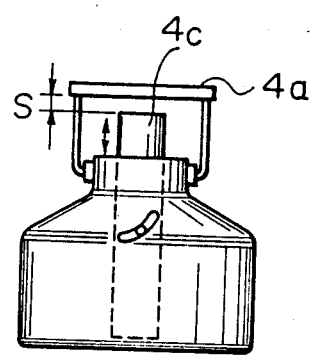

FIGS. 4G and 4H show still another modification. Two liquid chemical agent tanks 44g and 44h having retaining seats 414a and 414b with different depths with respect to an outer container 41d are prepared. By exchanging the liquid chemical agent tanks 44g and 44h, the relative vertical position of the wick 46 with respect to the heater 43 may be changed.

In each of the above-described modifications, the depth to which the wick is inserted into the heater is changed. Alternatively, wicks having different thickness may be inserted into different liquid chemical agent tanks and held thereby, so that by exchanging the liquid chemical agent tanks the space between the wick and heater is varied, as shown in FIGS. 4I(A) and 4I(B), or the sectional configurations of the wicks may be varied, as shown in FIGS. 4I(C) and 4I(D). The chemical agents in the different liquid chemical agent tanks in this embodiment may be either the same or different. In the former case, it is possible to change the amount of chemical agent evaporated, while in the latter case, it is possible to evaporate the amount of chemical agent in correspondence with the evaporation type of the respective chemical agent.

According to this embodiment, it is possible to change the position of the wick 46 with respect to the heater in the axial direction or the diametric direction, as well as the sectional configuration of the wick, by exchanging the liquid chemical agent tanks 44a, 44b, 44c, . . . with respect to the outer containers 41a, 41b, 41c, . . . , respectively. Accordingly, it is possible to appropriately select the heating area and obtain the optimum amount of chemical agent evaporated by appropriately selecting the liquid chemical agent tank in accordance with the state of use. It is also possible to change the period of use by changing the volume of the liquid chemical agent tanks 44a, 44b, 44c, . . .

Furthermore, since it is possible to fit the wick into each of the liquid chemical agent tanks in such a manner as to serve as a stopper, there is no danger of the liquid chemical agent leaking from the joint.

The present invention will be explained in greater detail by reference to the following examples.

EXAMPLES OF ANTIOXIDANTS

EXAMPLE 1

A raw material consisting of 8 parts by weight of gypsum, 5 parts by weight of clay, 2 parts by weight of diatomaceous earth and 0.4 part by weight of CMC was kneaded with one of the specific compounds shown in Table 2 and water, extrusion molded and dried to form a porous wick having a diameter of 7 mm and a length of 7 cm. The respective wicks obtained were mounted on the heat transpirer shown in FIG. 1. The liquid in the container was 50 ml of a mixed aliphatic saturated hydrocarbon solution having 14 to 17 carbon atoms and containing one of the chemical agents shown in Table 2.

The heater was energized to heat the upper side surface of the wick to 120° C., and the amount of insecticide which evaporated during one time of heating was measured. The results are shown in Table 3.

Evaporation amount: Vapor was trapped by a column filled with silica gel for a specified period of time at predetermined intervals, extracted with chloroform, condensed and subjected to quantitative analysis by a gas chromatograph.

TABLE 2

| Example No. | Antioxidant | | Insecticidal Agent | |
|---|---|---|---|---|
| | Name | Concentration (w/w %) | Name | Concentration (w/w %) |
| 1a | A | 0.05 | PA | 8 |
| 1b | A | 1.0 | PA | 8 |
| 1c | A | 0.05 | PB | 3 |
| 1d | A | 1.0 | PB | 3 |
| 1e | A | 0.02 | PE | 1 |
| 1f | A | 0.05 | PE | 1 |
| 1g | A | 1.0 | PE | 1 |
| 1h | A | 2.5 | PE | 1 |
| 1i | A | 0.3 | PH | 6 |
| 1j | A | 0.3 | PJ | 3 |
| 1k | A | 0.3 | PO | 3 |
| 1l | A | 0.3 | PP | 6 |
| 1m | C | 0.05 | PB | 3 |
| 1n | C | 1.0 | PB | 3 |
| 1o | C | 0.05 | PE | 1 |
| 1p | C | 1.0 | PE | 1 |
| 1q | I | 0.02 | PB | 3 |
| 1r | I | 0.5 | PB | 3 |
| 1s | I | 0.02 | PE | 1 |
| 1t | I | 0.5 | PE | 1 |
| 1u | J | 0.05 | PB | 3 |
| 1v | J | 1.0 | PB | 3 |
| 1w | J | 0.05 | PE | 1 |
| 1x | J | 1.0 | PE | 1 |

TABLE 3

| Example No. | Evaporation amount (mg/hr) Heating time | | | |
|---|---|---|---|---|
| | 100 hrs. | 200 hrs. | 300 hrs. | 400 hrs. |
| 1a | 3.43 | 3.44 | 3.31 | 3.26 |
| 1b | 3.25 | 3.26 | 3.17 | 3.14 |
| 1c | 2.14 | 2.15 | 2.07 | 2.02 |
| 1d | 1.89 | 1.87 | 1.80 | 1.76 |
| 1e | 0.89 | 0.87 | 0.86 | 0.83 |
| 1f | 0.78 | 0.79 | 0.77 | 0.75 |
| 1g | 0.57 | 0.57 | 0.54 | 0.52 |
| 1h | 0.44 | 0.41 | 0.39 | 0.38 |
| 1i | 4.15 | 4.14 | 4.09 | 3.97 |
| 1j | 1.82 | 1.80 | 1.81 | 1.75 |
| 1k | 2.31 | 2.28 | 2.24 | 2.19 |
| 1l | 3.72 | 3.74 | 3.64 | 3.59 |
| 1m | 2.05 | 2.03 | 2.00 | 1.95 |
| 1n | 1.87 | 1.86 | 1.82 | 1.78 |
| 1o | 0.88 | 0.87 | 0.85 | 0.81 |
| 1p | 0.59 | 0.60 | 0.58 | 0.55 |
| 1q | 1.99 | 1.95 | 1.92 | 1.86 |
| 1r | 1.75 | 1.73 | 1.68 | 1.64 |
| 1s | 0.76 | 0.75 | 0.71 | 0.67 |
| 1t | 0.57 | 0.59 | 0.55 | 0.48 |
| 1u | 2.07 | 2.05 | 2.01 | 2.00 |
| 1v | 1.89 | 1.88 | 1.85 | 1.83 |
| 1w | 0.83 | 0.82 | 0.79 | 0.78 |
| 1x | 0.64 | 0.62 | 0.61 | 0.59 |

As is obvious from the results, it was possible to evaporate the insecticidal agents stably for about 400 hours from the start of heating.

EXAMPLE 2

Example 1 was repeated except that the active ingredients shown in Table 4 were used in stead of those shown in Table 3. All of the active ingredients gave out fragrance stably for about 400 hours from the start of heating.

TABLE 4

| Example No. | Antioxidant | | Active Ingredient | |
|---|---|---|---|---|
| | Name | Concentration (w/w %) | Name | Concentration (w/w %) |
| 2a | B | 0.3 | Limonene | 0.5 |
| 2b | D | " | Menthol | " |
| 2c | E | " | Citronellal | " |
| 2d | F | " | Camphor | " |
| 2e | G | " | Coumarin | " |
| 2f | H | " | Citronella oil | " |

Although examples are not shown, when the chemical agents PC, PD, PF, PI, PK, PL, PM, PN, PQ, PR, PS, diethyl taluamide, etc. were tested in the same way as in Example 1, all of them evaporated stably over a long period.

COMPARATIVE EXAMPLES 101 to 104

A similar aliphatic saturated hydrocarbon solution to that employed in Example 1 was used and the evaporation amount was measured in the same way as in Example 1 except that the chemical agents and the amount of chemical agent added were changed as shown in Table 5. The results are shown in Table 6.

TABLE 5

| Example No. | Compound | | Chemical Agent | |
|---|---|---|---|---|
| | Name | Concentration (w/w %) | Name | Concentration (w/w %) |
| 101 | BHT | 0.5 | PB | 3 |
| 102 | " | 1.0 | PB | " |
| 103 | BHA | 0.5 | PN | " |
| 104 | " | 1.0 | PN | " |

TABLE 6

| Example No. | Evaporation amount (mg/hr) Heating time | | | |
|---|---|---|---|---|
| | 100 hrs. | 200 hrs. | 300 hrs. | 400 hrs. |
| 101 | 1.71 | 1.15 | 0.41 | 0.10 |
| 102 | 1.75 | 1.20 | 0.43 | 0.11 |
| 103 | 2.08 | 1.33 | 0.73 | 0.21 |
| 104 | 2.13 | 1.38 | 0.75 | 0.25 |

As is obvious from the results shown above, in the case of the wicks containing an antioxidant such as BHT and BHA, which evaporates at a heating temperature, the evaporation amount was greatly reduced by long-term heating, so that long-term stable evaporation of the liquid chemical agent was impossible.

EXAMPLES OF POROSITY

EXAMPLE 3

A mixture having the composition shown in Table 7 was kneaded with water, extrusion molded and dried to form a porous wick having a diameter of 7 mm and a length of 7 cm.

Thirty milliliters of a mixed aliphatic hydrocarbon solution having 14 to 17 carbon atoms was put into a 50 ml container such as that shown in FIG. 1, and each of the wicks obtained in the above-described way was inserted thereinto such that the wick was in close contact with the mouth portion of the container. The container was allowed to stand at 25° C. for 3 days. After the container was held at 50° C. for 1 hour, the ambient temperature lowered to 25° C. and the ambient pressure was reduced to 0.9 atm. After this state had been maintained for 30 minutes, the weight of the aliphatic hydrocarbon solution that leaked from the wick was measured. The results are shown in Table 8 together with the porosity of each wick.

TABLE 7

| Composition | No. 1 | No. 2 | No. 3 | No. 4 | No. 5 | No. 6 |
|---|---|---|---|---|---|---|
| Gypsum | 15 | — | — | 8 | 8 | — |
| Clay | — | 15 | 8 | 4 | 5 | 6 |
| Diatomaceous earth | — | — | — | 1 | — | — |
| Pearlite | — | — | — | 0.5 | 3 | 6 |
| Plastic powder | — | — | 2 | — | — | — |
| Wood powder | — | — | — | — | 1 | — |
| Activated charcoal | — | — | — | — | — | 1 |
| CMC | 1.2 | 0.8 | 0.5 | 0.3 | 0.4 | 1 |
| Starch | — | 1 | 3 | — | — | — |

TABLE 8

| Characteristic | No. 1 | No. 2 | No. 3 | No. 4 | No. 5 | No. 6 |
|---|---|---|---|---|---|---|
| Porosity (%) | 19 | 25 | 31 | 41 | 52 | 60 |
| Amount of leakage at 50° C. (mg) | 10 | 15 | 29 | 62 | 134 | 291 |
| Amount of leakage at 0.9 atm. (mg) | 8 | 13 | 24 | 55 | 117 | 270 |

As is obvious from the results, when the porosity exceeded 40%, a considerable amount of leakage was produced. The porosity was measured and calculated in the following way:

Porosity: A wick was put into a desiccator. After the desiccator had been evacuated substantially completely, an aliphatic saturated hydrocarbon was put into the desiccator and the wick was immersed therein. The pressure of the desiccator was restored to atmospheric pressure. The increment of weight of the wick was measured and the porosity was calculated from the following formula:

$$\text{porosity} = \frac{\text{increment of weigh of wick}}{\text{specific gravity of aliphatic saturated hydrocarbon}} \times \frac{100}{\text{volume of wick}}$$

COMPARATIVE EXAMPLE

The porosity and the amount of leakage of a wick used in a commercially available heat fumigation insect killing apparatus were measured in the same way as in Example 3. The porosity was 65%, the amount of leakage at 50° C. was mg, and the amount of leakage at 0.9 atm. was 259 mg.

EXAMPLE 4

A raw material consisting of 7 parts by weight of gypsum, 5 parts by weight of clay, 2 parts by weight of diatomaceous earth and 0.3 part by weight of CMC was formed into a porous wick having a diameter of 7 mm and a length of 7 cm. The porosity was 35%. The wick was mounted on the heat transpirer shown in FIG. 1. The liquid in the container was 10 ml of a mixed aliphatic saturated hydrocarbon solution having 14 to 17 carbon atoms and containing a chemical agent shown in Table 9. The heater was energized to heat the upper side surface of the wick to 120° C., and the evaporation amount of insecticide per heating time and the total effective evaporation ratio were measured. The results are shown in Table 9. The evaporation amount and the total effective evaporation ratio were measured in the following way:

Evaporation amount: Vapor was continuously trapped by a column filled with silica gel at predetermined intervals, extracted with chloroform, condensed and subjected to quantitative analysis by a gas chromatograph. The total sum of the thus-obtained values was divided by the total evaporation time.

Total effective evaporation ratio (recovery): The total evaporation amount which gives an evaporation amount per unit of time of substantially 0 was obtained in the above-described way, and the amount of effective ingredient (A mg) in the solution remaining in the container and the amount of effective ingredient remaining in the wick (B mg=concentration of the solution remaining in the container × increment of weight of the wick) were obtained. By using the amount of effective ingredient (C mg) before heating, the total effective evaporation ratio was calculated using the following formula:

$$\frac{\text{total effective}}{\text{evaporation ratio (\%)}} = \frac{\text{total evaporation amount}}{C - (A + B)} \times 100$$

TABLE 9

| Chemical agent | | Total evaporation amount (mg/hr) | Total effective evaporation ratio (%) |
|---|---|---|---|
| Name | Concentration (w/w %) | | |
| Pynamin | 8 | 3.62 | 81 |
| Pynaminforte | 3 | 1.76 | 86 |
| Prallethrin | 0.8 | 0.48 | 89 |

COMPARATIVE EXAMPLE

A raw material consisting of 6 parts by weight of clay, 8 parts by weight of pearlite, 1 part by weight of starch and 0.3 part by weight of CMC was formed into a porous wick having a porosity of 55%. The evaporation amount and the total effective evaporation ratio of chemical agent were measured in the same way as in Example 4. The results are shown in Table 10.

TABLE 10

| Chemical agent | | Total evaporation amount (mg/hr) | Total effective evaporation ratio (%) |
|---|---|---|---|
| Name | Concentration (w/w %) | | |
| Pynamin | 8 | 5.42 | 72 |
| Pynaminforte | 3 | 3.26 | 74 |
| Prallethrin | 0.8 | 1.13 | 78 |

As is obvious from the results given above, when the porosity of the wick was too high, a much larger amount of chemical agent than necessary for killing mosquitoes was evaporated, and the total effective evaporation ratio was reduced. Therefore, the usable life of the apparatus was short, and effective transpiration over a long period was impossible.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. In an apparatus for transpiring by heating a solution of an insecticide dissolved in a solvent, which comprises
a container having said solution therein, a wick a part of which is immersed in the solution, and a heater for heating an upper portion of the wick for transpiring the solution drawn up the wick, the improvement wherein
said wick is molded from a mixture comprising a first component selected from the group consisting of an inorganic powder, organic powder or mixture thereof; a binding agent; and at least one antioxidant which is substantially non-evaporative at a heating temperature.

2. An apparatus according to claim 1, wherein said first component is inorganic powder and said inorganic powder is selected from the group consisting of clay, talc, kaolin, diatomaceous earth, gypsum, pearlite, bentonite, volcanic stone, acid clay, glass fiber and asbestos.

3. An apparatus according to claim 1, wherein said first component is organic powder and said organic powder is selected from wood powder, activated charcoal, cellulose, pulp, linter and polymeric resins.

4. An apparatus according to claim 1, wherein said binding agent is selected from the group consisting of carboxymethylcellulose, starch, acacia gum, gelatin and polyvinyl alcohol.

5. An apparatus according to claim 1, wherein said solvent is an aliphatic saturated hydrocarbon solvent having 12 to 18 carbon atoms.

6. An apparatus according to claim 1, wherein said wick is a porous body having a porosity of 25 to 40%.

7. An apparatus according to claim 1, wherein said apparatus comprises an apparatus body which accommodates said container having said wick for drawing up said liquid chemical contained in said container, and wherein said apparatus body has an opening on the side of the body so that at least a part of the body portion of said container is exposed to an atmosphere outside the apparatus.

8. An apparatus according to claim 7, wherein said apparatus body further comprises a lighting means for illuminating the liquid surface of said bottle.

9. An apparatus according to claim 1, wherein said apparatus further comprises an outer container having a transpiration hole on the upper surface of the container and said heater is positioned under said transpiration hole and secured to the container; and a plurality of liquid chemical tanks which are removably accommodated in the lower portion inside said outer container and from which a wick is projected opposite said heater, said plurality of liquid chemical tanks having a structure which enables the positional relationship between said wick and said heater to be changed in a vertical direction or in a radial direction in a state in which said liquid chemical tanks are accommodated in said outer container.

10. An apparatus according to claim 1 wherein said solution is drawn up a wick part of which is immersed in said solution in said container, and said solution is caused to transpire by heating the upper portion of said wick by means of said heater, further comprising an apparatus body comprising a main body for accommodating said container and a cover which is disposed above said heater integrally with or separately from said main body and which has a transpiration hole substantially above said heater; and a heat receiving portion having vent holes at least at the center and around said heat receiving portion, said portion being provided within said transpiration hole such that said heat receiving portion is situated at a lower position than the upper surface of said transpiration hole and at least a part of said heat receiving portion is situated above said heater.

11. An apparatus according to claim 1, wherein said antioxidant is selected from the group consisting of 2,2'-methylene-bis(4-ethyl-6-t-butylphenol); 2,2'-methylene-bis(4-methyl-6-t-butylphenol); 4,4'-methylene-bis(2-methyl-6-t-butylphenol); 4,4'-butylidene-bis(3-methyl-6-t-butylphenol); 4,4'-thiobis(3-methyl-6-t-butylphenol); 4,4'-methylene-bis(2,6-di-t-butylphenol); stearyl-8-(3,5-di-t-butyl-4-hydroxyphenyl)propionate; 1,3,5-trimethyl-2,4,6-tris(3,5-di-t-butyl-4-hydroxybenzyl)benzene; 1,1,3-tris(2-methyl-5-t-butyl-4-hydroxyphenyl)butane; tetrakis[methylene(3,5-di-t-butyl-4-hydroxycinnamate)]methane; N,N'-hexamethylenebis(3,5-di-t-butyl-4-hydroxycinnamate)]methane; N,N'-hexamethylenebis(3,5-di-t-butyl-4-hydroxy-hydrocinnamamide); 1,6-hexanediol-bis-[3-(3,5-di-t-butyl-4-hydroxyphenyl)propionate[; triethyleneglycol-bis-[3-(3-t-butyl-5-methyl-4-hydroxyphenyl)propionate]; 2,2-thio-diethylenebis[3-(3,5-di-t-butyl-4-hydroxyphenyl)propionate]; N,N'-bis[3-(3,5-di-t-butyl-4-hydroxyphenyl)propionyl]hydrazine; tris-(3,5-di-t-butyl-4-hydroxybenzyl)-isocyanurate; 2,4-bis-(n-octylchio)-6-(4-hydroxy-3,5-di-t-butylanilino)-1,3,5-triazine; 2,2-chiobis(4-methyl-6-t-butylphenol); and 3,5-di-t-butyl-4-hydroxybenzylphosphonate diethylester.

12. An apparatus according to claim 1 wherein the concentration of the insecticide in the solution is in the range of 0.5 to 8% by weight.

13. An apparatus according to claim 1 wherein the concentration of the antioxidant in the wick is in the range of 0.02 to 3% by weight.

14. An apparatus according to claim 13 wherein the concentration of the antioxidant is in the range of 0.02 to 1% by weight.

* * * * *